US008741283B2

(12) United States Patent
Filpula et al.

(10) Patent No.: US 8,741,283 B2
(45) Date of Patent: Jun. 3, 2014

(54) ADENOSINE DEAMINASE ANTICANCER THERAPY

(75) Inventors: David R. Filpula, Piscataway, NJ (US); Puja Sapra, Edison, NJ (US)

(73) Assignee: Sigma-Tau Rare Diseases, S.A., Funchal (PT)

( * ) Notice: Subject to any disclaimer, the term of this patent is extended or adjusted under 35 U.S.C. 154(b) by 506 days.

(21) Appl. No.: 12/105,682

(22) Filed: Apr. 18, 2008

(65) Prior Publication Data

US 2009/0047270 A1 Feb. 19, 2009

Related U.S. Application Data

(60) Provisional application No. 60/913,039, filed on Apr. 20, 2007.

(51) Int. Cl.
*A61K 38/44* (2006.01)
*C12N 9/00* (2006.01)
*C12N 9/78* (2006.01)
*C12N 1/20* (2006.01)
*C12N 15/00* (2006.01)

(52) U.S. Cl.
USPC ....... 424/94.4; 435/183; 435/227; 435/252.3; 435/320.1; 536/23.2

(58) Field of Classification Search
None
See application file for complete search history.

(56) References Cited

U.S. PATENT DOCUMENTS

| | | | |
|---|---|---|---|
| 5,122,614 A | 6/1992 | Zalipsky |
| 5,324,844 A | 6/1994 | Zalipsky |
| 5,346,823 A | 9/1994 | Estell et al. |
| 5,349,001 A | 9/1994 | Greenwald et al. |
| 5,612,460 A | 3/1997 | Zalipsky |
| 5,643,575 A | 7/1997 | Martinez et al. |
| 5,681,567 A | 10/1997 | Martinez et al. |
| 5,756,593 A | 5/1998 | Martinez et al. |
| 5,808,096 A | 9/1998 | Zalipsky |
| 5,919,455 A | 7/1999 | Greenwald et al. |
| 5,965,119 A | 10/1999 | Greenwald et al. |
| 6,113,906 A | 9/2000 | Greenwald et al. |
| 6,153,655 A | 11/2000 | Martinez et al. |
| 6,180,095 B1 | 1/2001 | Greenwald et al. |
| 6,251,382 B1 | 6/2001 | Greenwald et al. |
| 6,303,569 B1 | 10/2001 | Greenwald et al. |
| 6,395,266 B1 | 5/2002 | Martinez et al. |
| 6,579,857 B1 | 6/2003 | Lind et al. |
| 6,624,142 B2 | 9/2003 | Greenwald et al. |
| 6,638,499 B2 | 10/2003 | Martinez et al. |
| 6,720,306 B2 | 4/2004 | Greenwald et al. |
| 6,824,766 B2 | 11/2004 | Greenwald et al. |
| 7,087,229 B2 | 8/2006 | Zhao et al. |
| 7,122,189 B2 | 10/2006 | Zhao et al. |
| 7,413,738 B2 | 8/2008 | Zhao et al. |
| 2002/0088017 A1 | 7/2002 | Kellems et al. |
| 2002/0156248 A1 | 10/2002 | Filpula et al. |
| 2006/0286065 A1 | 12/2006 | Zhao et al. |
| 2007/0078219 A1 | 4/2007 | Zhao et al. |
| 2007/0166276 A1 | 7/2007 | Zhao et al. |
| 2007/0173615 A1 | 7/2007 | Zhao et al. |
| 2008/0159964 A1 | 7/2008 | Blackburn et al. |
| 2008/0249260 A1 | 10/2008 | Zhao et al. |

FOREIGN PATENT DOCUMENTS

| | | |
|---|---|---|
| JP | 2005-516917 A | 6/2005 |
| WO | 0126625 | 4/2001 |
| WO | 02077233 | 10/2002 |
| WO | 03/050241 A2 | 6/2003 |
| WO | 03045436 | 6/2003 |
| WO | 03050241 A2 | 6/2003 |
| WO | 2007149686 A2 | 12/2007 |
| WO | 2008034119 A2 | 3/2008 |
| WO | 2008131208 A1 | 10/2008 |

OTHER PUBLICATIONS

Barugel et al. Expert Rev Anticancer Ther. Dec. 2009;9(12):1829-47 (Abstract).*
Kelly et al. J Pharm Biomed Anal. Aug. 1996;14(11):1513-19.*
European Search Report issued in EP 08754910.1 and dated Nov. 2, 2010.
First Office Action issued in counterpart Russian Application No. 2009142817, with English language translation.
Second Office Action issued in counterpart Russian Application No. 2009142817, with English language translation.
Office Action issued in counterpart Japanese Application No. 2010-504262, with English language translation.
Davis, et al., "PEG-Adenosine Deaminase and PEG-Asparaginase," Advances in Experimental Medicine and Biology, vol. 519, pp. 51-58 (2003).
Lelievre, et al., "Adenosine modulates cell proliferation in human colonic adenocarcinoma. I. Possible involvement of adenosine A1 receptor subtypes in HT29 cells," European Journal of Pharmacology, vol. 341, pp. 289-297 (1998).
Final Office Action issued in U.S. Appl. No. 12/105,913 and dated Nov. 9, 2010.
Dieters et al., Site-specific PEGylation of proteins containing unnatural amino acids, Bioorganic & Medicinal Chemistry Letters 14:5743-5745, 2004.
First Office Action issued in counterpart Russian Application No. 2009142817, with English language translation, (Aug. 29, 2012).
Second Office Action issued in counterpart Russian Application No. 2009142817, with English language translation, (Oct. 4, 2012).
Chissov, et al., Oncology ed., GEOTAR-Media, pp. 49-50, 2007 (Russian language reference). No translation available.
Kaufman, et al., "Cerebral Lymphoma in an Adenosine Deaminase-Deficient Patient With Severe Combined Immunodeficiency Receiving Polyethylene Glycol-Conjugated Adenosine Deaminase," Official Journal of the American Academy of Pediatrics, vol. 116, No. 6, pp. e876-e879, Dec. 6, 2005.

(Continued)

Primary Examiner — Christian Fronda
(74) Attorney, Agent, or Firm — Lucas & Mercanti, LLP

(57) ABSTRACT

What is provided is a method of treating a patient having a tumor comprising administering an effective amount of adenosine deaminase, preferably polyalkylene oxide conjugated, to a patient in need thereof.

19 Claims, No Drawings

(56) References Cited

OTHER PUBLICATIONS

Nikiti et al., "Pegylated medicinal preparations: modern state of problem and perspectives, Mar. 2003 [on line Apr. 4, 2012]" (Russian language reference). No translation is available, but an English language summary in the form of a letter from the Russian associate is attached to the Russian language article.

International Search Report and Written Opinion dated Jul. 28, 2008 issued in PCT/US08/60733.

Barcz et al., Adenosine receptor antagonism causes inhibition of angiogenic activity of human ovarian cancer cells, Oncology Reports, 7:1285-1291, 2000.

Adair et al., Growth regulation of the vascular system: an emerging role of adenosine, the American Journal of Physiology-Regulatory, Integrative and Comparative Physiology, 289:283-296, 2005.

Mujoomdar et al., Adenosine stimulation of the proliferation of colorectal carcinoma cell lines Roles of cell density and adenosine metabolism, Biochemical Pharmacology, 66:1737-1747, 2003.

Asmar et al., Effect of administration of adenosine aminohydrolase from *Aspergillus oryzae* on the growth of cancer cells (Abstract No. 73), Proceedings of the American Association for Cancer Research, 7:19, 1966.

Parkman et al., Gene therapy for adenosine deaminase deficiency, Ann. Rev. Med., 51:33-47, 2000.

NOF Corp. Drug Delivery System catalog, Ver.8, Apr. 2006.

Shearwater Corporation's 2001 catalog, Polyethylene Glycol and Derivatives for Biomedical Application.

Blay et al., The extracellular fluid of solid carcinomas contains immunosuppressive concentrations of adenosine, Cancer Research, 57:2602-2605, 1997.

Spychala J., Tumor-promoting functions of adenosine, Pharmacology & Therapeutics, 87:161-173, 2000.

Stikovsky et al., Regulation of immune cells by local-tissue oxygen tension: HIF1a and adenosine receptors, Nature Reviews Immunology, 5:712-721, 2005.

Merighi et al., A3 adenosine receptors modulate hypoxia-inducible factor-1a expression in human A375 melanoma cells, Neoplasia, 7:894-903, 2005.

Koh et al., HAF, a novel E3-ubiquitin ligase, binds and ubiquitinates, HIF-1a leading to its oxygen-independent degradation, Mol. Cell. Biol., 10, 2008.

Package Insert of ADAGEN™ (Enzon, Inc.), (2008).

\* cited by examiner

ADENOSINE DEAMINASE ANTICANCER THERAPY

CROSS-REFERENCE TO RELATED APPLICATION

This application claims the benefit of priority from U.S. Provisional Patent Application Ser. Nos. 60/913,039 filed Apr. 20, 2007, the contents of which are incorporated herein by reference.

FIELD OF THE INVENTION

The invention provides new methods of treating and inhibiting tumors, and especially malignant solid tumors, by administering adenosine deaminase in order to reduce tissue levels of adenosine and deoxyadenosine.

BACKGROUND OF THE INVENTION

A tumor is an abnormal benign or malignant growth of cells or tissue that arises from uncontrolled cellular proliferation. A malignant tumor is a one that spreads from its site of origin, and is also art-known as a cancer. Thus, tumors and cancers are a family of diseases sharing the common property of uncontrolled or inappropriate cell growth. Broadly, malignant tumors are either blood derived tumors, such as leukemia, or solid tumors. Blood derived malignant tumors generally circulate in the blood, but solid malignant tumors spread throughout the body from a primary tumor. The distributed tumor cells then have the potential to develop into multiple secondary tumors, in a process of metastasis. In order for a solid tumor to undergo such a metastatic spread, solid tumor cells must escape from the primary or original tumor, enter the blood stream or lymphatic system, and from there invade the tissue of other organs, where they multiply and form new tumors. Metastasis is a complex multi-step process that involves changes in tumor cell adhesion and motility, secretion of proteolytic enzymes, chemoattractants, and proteoglycans and other factors. In addition, angiogeniesis, or the formation of new blood vessels, is also a vital step in the metastatic process (Folkman, 1995, *Nature Medicine* 1:27-31).

The immune system has also been shown to inhibit the metastasis of such malignant tumor cells, and it has been reported that adenosine, in turn, may inhibit such immune protective reactions. For example, Loshkin et al., (2006, *Cancer Res.* 66: 7758-7765) report that adenosine inhibits activation and cytokine production in killer T cells. Adenosine negatively impacts other immune function, including both cellular elements and inflammatory functions (see, e.g., the reviews by Spychala, 2000, *Pharmacology & Therapeutics* 87: 161-173 and by Sitkovesky et al., 2005 *Nature Reviews Immunology* 5: 713-721). Sitkovesky et al., in WO 03/050241, published Jun. 19, 2003, also described methods for increasing an immune response to an antigen and for treating tumors, by administering an adenosine receptor antagonist, that can include adenosine deaminase.

It has also been shown that adenosine promotes tumor cell migration and angiogenesis (Barcz et al., 2000, *Oncol. Rep.* 7(6): 1285-91; Adair, 2005 *Am J Physiol Regul Integr Comp Physiol* 289: R283-R296) and that adenosine stimulates the proliferation of colon cancer cells (Mujoomdar et al. 2003, *Biochemical Pharmacology* 66 1737-1747). It has also been reported by Asmar et al., 1966, *Proc. Am. Assoc. Cancer Res.* (Abstract No. 73) that the growth of certain tumor cells was inhibited, by injection of ADA, by over 50% in a mouse ascites model. These were lymphatic leukemias L1210 and L4946, lymphosarcoma 6C3HED, mammary adenocarcinoma TA3, and Ehrlich carcinoma E2. In the same Abstract, an adenocarcinoma 755 was reported to be twice as resistant to and a sarcoma 180 was completely resistant to the effect. WO03050241 A2 describes the effects of an inhibitor of adenosine receptors on B16 melanoma cells. While WO03050241A2 mentions ADA as an inhibitor of adenosine, there is no specific description for applying ADA to the treatment of specific cancers, and particularly ovarian cancer and prostate cancer.

Thus, it seems that for some tumors, the presence of adenosine provides a "go" signal for tumor proliferation and for tumor angiogeniesis, and a "stop" signal for the killer T cells which would normally kill these tumors.

In contrast to the above-discussed findings, Lind, et al. (U.S. Pat. No. 6,579,857) have reported that adenosine, in combination with an inhibitor of the enzyme adenosine deaminase, and/or in combination with an anticancer agent such as coformycin, is useful in a method for potentiating cell death in neoplastic cells of epithelial origin. Thus, this reference suggests that the role of adenosine in cancer is more complex and unsettled.

As noted above, an agent for reducing endogenous adenosine levels is the enzyme adenosine deaminase. Adenosine deaminase ("ADA"), designated as EC 3.5.4.4, is an important enzyme of the purine salvage pathway. ADA converts either adenosine or deoxyadenosine, in the presence of water, into inosine or deoxyinosine and ammonia. It is known that individuals who harbor deleterious mutations in the ADA gene can develop varying degrees of an immunodeficiency disorder, from mild to severe, i.e. severe combined immunodeficiency disorder ("SCID"). SCID has been confirmed to result from the toxic accumulation of the enzyme substrates, adenosine and deoxyadenosine, in immature lymphoid cells. The onset of the disorder can range from early childhood to adults, depending on the mutations inherited. Deficiencies of ADA are one of the leading causes of SCID, in children, and is one of the leading targets for gene therapy approaches (R. Parkman et al., 2000, Gene therapy for adenosine deaminase deficiency, *Ann. Rev. Med.*, 51:33-47).

Previously, ADA has been commercially isolated from bovine sources and employed in treating a number of disorders, including SCID, in the form of a bovine ADA conjugated to polyethylene glycol ("PEG") polymer. PEGylated ADA for medical use is commercially available from Enzon Pharmaceuticals, Inc. as ADAGEN®, PEGylated ADA. The conjugation of a PEG moiety to ADA allows the enzyme to achieve its full therapeutic effect by increasing the circulating life and rendering the ADA substantially non-antigenic, in order to minimize the potential for immunogenic reactions. It is also possible to produce recombinant human or bovine ADA enzymes for use in a conjugated form, as described by co-owned U.S. patent application Ser. No. 11/738,012, entitled "Stabilized Proteins", and co-owned U.S. application Ser. No. 12/105,913, entitled "Stable Recombinant Adenosine Deaminase", filed on even date herewith and claiming the benefit of priority from U.S. Patent Application Ser. No. 60/913,009, and both incorporated by reference herein in their entireties.

Thus, there is a longstanding need in the art for new and improved methods of treating or inhibiting the growth, spread and development of cancers.

SUMMARY OF THE INVENTION

Accordingly, the invention provides a method of treating a patient having a tumor comprising administering an effective amount of ADA to the patient in need thereof. An effective amount is that which is readily determined by one of ordinary skill in the art to reduce tissue levels of adenosine or deoxyadenosine in the patient, and wherein growth or spread of the tumor is inhibited by substantially reduced tissue levels of adenosine in the patient. The route of administration is a route such as subcutaneous, intravenous, intramuscular, intrathecal, intraperitoneal, inhalation and transurethral.

The tumor can be malignant or nonmalignant, and is preferably a solid tumor, e.g., a tumor such as a prostate tumor, an ovarian cancer and/or a colorectal cancer.

The adenosine deaminase is preferably conjugated to a substantially non-antigenic polymer, such as a polyalkylene oxide (PAC). The PAO preferably ranges in size from about 4,000 to about 45,000 Daltons. The PAO is preferably a polyethylene glycol ("PEG"). The molar ratio of ADA to polymer can be 1:1, or can be two or more ADA molecules per polymer, or more preferably, provides for from about 1 to about 20 polymer molecules (i.e. 11-18 PEG strands) per ADA molecule.

The polymer-conjugated ADA is preferably administered in a dose ranging from about 10 U to about 30 U per kg or more and for a sufficient period of time to maintain inhibition of the tumor, e.g., from about 1 to about 20 days, or longer.

The amount of adenosine deaminase that is administered is effective to substantially reduce tissue levels of adenosine or deoxyadenosine in the patient, and wherein growth or spread of the tumor is inhibited by substantially reduced tissue levels of adenosine in said patient. This is, for example, a dose of adenosine deaminase ranging from about 10 U to about 30 U per kg. The dose is repeated for a sufficient period of time to maintain inhibition of the tumor, e.g., from about 1 to about 20 days, or longer. The dose is administered by any convenient route such as subcutaneous, intravenous, intramuscular, intrathecal, intraperitoneal, inhalation and transurethral.

The adenosine deaminase is optionally purified from a bovine source or is a recombinant adenosine deaminase. The recombinant adenosine deaminase is, for example, recombinant bovine adenosine deaminase (Ser74-rbADA) comprising SEQ ID NO: 1, recombinant human adenosine deaminase (Ser74-rhADA) comprising SEQ ID NO: 3 and recombinant bovine adenosine deaminase comprising SEQ ID NO: 5 and/ or variations or polymorphisms thereof. Recombinantly produced bovine adenosine deaminase, e.g., SEQ ID NO: 5, is optionally capped at Cys74 for stability in an aqueous medium.

For purposes of the present invention, the term "residue" shall be understood to mean that portion of a compound, to which it refers, e.g., PEG, ADA, amino acid, etc. that remains after it has undergone a substitution reaction with another compound.

For purposes of the present invention, the term "polymeric residue", e.g., "PEG residue", shall each be understood to mean that portion of the polymer or PEG which remains after it has undergone a reaction with other compounds, moieties, etc.

For purposes of the present invention, the term "alkyl" as used herein refers to a saturated aliphatic hydrocarbon, including straight-chain, branched-chain, and cyclic alkyl groups. The term "alkyl" also includes alkyl-thio-alkyl, alkoxyalkyl, cycloalkylalkyl, heterocycloalkyl, and $C_{1-6}$ alkylcarbonylalkyl groups. Preferably, the alkyl group has 1 to 12 carbons. More preferably, it is a lower alkyl of from about 1 to 7 carbons, yet more preferably about 1 to 4 carbons. The alkyl group can be substituted or unsubstituted. When substituted, the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups.

For purposes of the present invention, the term "substituted" as used herein refers to adding or replacing one or more atoms contained within a functional group or compound with one of the moieties from the group of halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ alkylcarbonylalkyl, aryl, and amino groups.

For purposes of the present invention, the term "alkenyl" refers to groups containing at least one carbon-carbon double bond, including straight-chain, branched-chain, and cyclic groups. Preferably, the alkenyl group has about 2 to 12 carbons. More preferably, it is a lower alkenyl of from about 2 to 7 carbons, yet more preferably about 2 to 4 carbons. The alkenyl group can be substituted or unsubstituted. When substituted the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups.

For purposes of the present invention, the term "alkynyl" refers to groups containing at least one carbon-carbon triple bond, including straight-chain, branched-chain, and cyclic groups. Preferably, the alkynyl group has about 2 to 12 carbons. More preferably, it is a lower alkynyl of from about 2 to 7 carbons, yet more preferably about 2 to 4 carbons. The alkynyl group can be substituted or unsubstituted. When substituted the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups. Examples of "alkynyl" include propargyl, propyne, and 3-hexyne.

For purposes of the present invention, the term "aryl" refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

For purposes of the present invention, the term "cycloalkyl" refers to a $C_{3-8}$ cyclic hydrocarbon. Examples of cycloalkyl include cyclopropyl, cyclobutyl, cyclopentyl, cyclohexyl, cycloheptyl and cyclooctyl.

For purposes of the present invention, the term "cycloalkenyl" refers to a $C_{3-8}$ cyclic hydrocarbon containing at least one carbon-carbon double bond. Examples of cycloalkenyl include cyclopentenyl, cyclopentadienyl, cyclohexenyl, 1,3-cyclohexadienyl, cycloheptenyl, cycloheptatrienyl, and cyclooctenyl.

For purposes of the present invention, the term "cycloalkylalkyl" refers to an alkyl group substituted with a $C_{3-8}$ cycloalkyl group. Examples of cycloalkylalkyl groups include cyclopropylmethyl and cyclopentylethyl.

For purposes of the present invention, the term "alkoxy" refers to an alkyl group of indicated number of carbon atoms attached to the parent molecular moiety through an oxygen bridge. Examples of alkoxy groups include, for example, methoxy, ethoxy, propoxy and isopropoxy.

For purposes of the present invention, an "alkylaryl" group refers to an aryl group substituted with an alkyl group.

For purposes of the present invention, an "aralkyl" group refers to an alkyl croup substituted with an aryl group.

For purposes of the present invention, the term "alkoxyalkyl" group refers to an alkyl group substituted with an alkyloxy group.

For purposes of the present invention, the term "alkyl-thioalkyl" refers to an alkyl-S-alkyl thioether, for example methylthiomethyl or methylthioethyl.

For purposes of the present invention, the term "amino" refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

For purposes of the present invention, the term n alkylcarbonyl refers to a carbonyl group substituted with alkyl group.

For purposes of the present invention, the terms "halogen' or "halo" refer to fluorine, chlorine, bromine, and iodine.

For purposes of the present invention, the term "heterocycloalkyl" refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrrolidinyl.

For purposes of the present invention, the term "heteroaryl" refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

For purposes of the present invention, the term "heteroatom" refers to nitrogen, oxygen, and sulfur.

In some embodiments, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo phenyl; aralkyls include moieties such as tolyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo shall be understood to include fluoro, chloro, iodo and bromo.

For purposes of the present invention, "positive integer" shall be understood to include an integer equal to or greater than 1 and as will be understood by those of ordinary skill to be within the realm of reasonableness by the artisan of ordinary skill.

For purposes of the present invention, the term "linked" shall be understood to include covalent (preferably) or non-covalent attachment of one group to another, i.e., as a result of a chemical reaction.

The terms "effective amounts" and "sufficient amounts" for purposes of the present invention shall mean an amount which achieves a desired effect or therapeutic effect as such effect is understood by those of ordinary skill in the art.

For purposes of the present invention, the term "adenosine" shall be understood to include the nucleosides adenosine and deoxyadenosine. Adenosine also includes adenosine and deoxyadenosine present in the form of AMP, ADP, ATP, dAMP, dADP or dATP.

For purposes of the present invention, "adenosine-mediated tumor" or "adenosine deaminase-responsive tumor" shall be understood as broadly including any types of tumors which benefit from the administration of ADA, or active fraction thereof, etc., regardless of the route of administration.

For purposes of the present invention, "treatment of adenosine-mediated tumor" or "treatment of adenosine deaminase-responsive tumor" or "inhibition of adenosine-mediated tumor growth" or "inhibition of adenosine deaminase-responsive tumor growth" shall be understood to mean that symptoms or conditions are minimized or attenuated when compared to that observed in the absence of the ADA treatment. The treated conditions can be confirmed by, for example, tumor growth inhibition and/or decrease in adenosine levels in cancer cells or tissues.

Broadly speaking, successful treatment shall be deemed to occur when the desired clinical response is obtained. For example, successful treatment can be defined by obtaining e.g., 10% or higher (i.e. 20% 30%, 40%) tumor growth inhibition. Alternatively, successful treatment can be defined by obtaining at least 20% or preferably 30%, more preferably 40% or higher (i.e., 50% or 80%) decrease in adenosine levels in cancer cells or tissues, including other clinical markers contemplated by the artisan in the field, when compared to that observed in the absence of the ADA treatment described herein.

Further, the use of singular terms for convenience in description is in no way intended to be so limiting. Thus, for example, reference to a composition comprising an enzyme refers to one or more molecules of that enzyme. It is also to be understood that this invention is not limited to the particular configurations, process steps, and materials disclosed herein as such configurations, process steps, and materials may vary somewhat.

It is also to be understood that the terminology employed herein is used for the purpose of describing particular embodiments only and is not intended to be limiting, since the scope of the present invention will be limited by the appended claims and equivalents thereof.

DETAILED DESCRIPTION OF THE INVENTION

Accordingly, the invention provides for new methods of treating tumors, including cancers, by administering ADA enzyme to a patient in need thereof in an amount, and for a duration sufficient to reduce the amount of adenosine present in the tissues and/or body fluids of the patient. Preferably, the ADA enzyme is polymer conjugated. For those tumors that depend upon the presence of adenosine for growth, metastatic spread and/or for protection from the patient's immune system, a sufficient reduction in endogenous adenosine will limit or prevent cancer growth, metastatic spread and/or allow the normal operation of antitumor activity by the patient's immune system.

It is also contemplated that the inventive ADA treatment of tumors is optionally conducted in combination or coordination with one or more other appropriate art-known anti-cancer treatment methods and agents, as discussed in greater detail herein below. The combination treatment of the present invention includes administering an effective amount of the compounds described herein alone or in combination, simultaneously or sequentially, with a second chemotherapeutic agent.

Exemplary art-known anti-cancer agents for such combination treatments include, e.g., Taxol™, bevacizumab (Avastin®), vincristine, vinblastine, neomycin, combretastatin(s), podophyllotoxin(s), TNF-alpha, angiostatin, endostatin, vasculostatin, alpha$_v$-beta$_3$ antagonists, calcium ionophores, calcium-flux inducing agents, any derivative or prodrug thereof.

The additional anti-cancer agents also include chemotherapeutic agents, radiotherapeutic agents, cytokines, anti-angiogenic agents, apoptosis-inducing agents or anti-cancer immunotoxins or coaguligands. One such immunotoxin is e.g. Erbitux® (cetuximab). "Chemotherapeutic agents", as used herein, refer to classical chemotherapeutic agents or drugs used in the treatment of malignancies. This term is used for simplicity notwithstanding the fact that other compounds may be technically described as chemotherapeutic agents in that they exert an anti-cancer effect. However, "chemotherapeutic" has come to have a distinct meaning in the art and is being used according to this standard meaning.

Thus, the inventive method can be employed in combination with one or more chemotherapeutic agents known to be effective in treating cancer, including but not limited to, 5-azacytidine, 5-fluorouracil, optionally in combination with leucovorin, 5-fluorodeoxyuridine, 6-mercaptopurine, 6-thioguanine, mitoxantrone, aziridinylbenzoquinone (AZQ), Carmustine (BCNU or BCNU from Bristol-Myers Squibb), bleomycin, carboplatin (CBDCA), Lomustine (CCNU), methyl-CCNU or MeCCNU, chlorambucil, chlorodeoxyadenosine, cisplatin, cyclophosphamide, cytarabine, dactinomycin, daunorubicin, deoxycoformycin, doxorubicin, doxycoformycin, DTIC (dacarbazine), epirubicin, etoposide (VP-16), fludarabine, hexamethylmelamine, hydroxyurea, idarubicin, ifosfamide, ifosfamide and mesna, levamisol, N-acetylcysteine ("NAC"), 1-phenylalanine mustard, 4'-(9-acridinylamino)methanesulfon-m-anisidide ("mAMSA"), art-known inhibitors of multiple drug resistance (ie., MDR inhibitors), melphalan, methotrexate, optionally in combination with leucovorin, mithramycin, mitomycin-c, inhibitors of multidrug resistance related protein ("MRP" inhibitors), paclitaxel, procarbazine, streptozotocin, N,N'N'-triethylenethiophosphoramide ("thioTEPA"), inhibitors of topoisomerase I and/or topoisomerase II, taxol, vinblastine, vincristein, vincristine, vindesine, teniposide (VM-26®), and others too numerous to mention.

Other methods of treating cancer contemplated to be employed in combination with the methods of the invention include irradiation with X-rays, gamma rays whether directly or with tomographic targeting, treatment of cancerous tissues with implanted radioactive pellets or "seeds," neutron beam irradiation of tissues primed with boron compounds, and/or other types of art-known particle beam therapy.

Further antitumor or anticancer agents (antineoplastic agents) that are optionally administered in combination or coordination with the instant inventive methods include those described by "GOODMAN AND GILMAN'S, THE PHARMACOLOGICAL BASIS OF THERAPEUTICS", TENTH EDITION, Eds. Hardman and Limbird, incorporated by reference herein in its entirety.

In order to better appreciate the invention, the following terms are defined.

Reference to "adenosine" herein also encompasses deoxyadenosine, and art-known variations and derivatives thereof present in vivo, unless otherwise specified.

Reference to adenosine deaminase or ADA includes any art-known form of the enzyme, including purified natural enzyme, e.g., purified natural ADA, recombinant human or bovine ADA and variations, polymorphisms, and derivatives thereof. ADA enzyme purified from bovine sources has a sequence according to SEQ ID NO: 5, with the Cys 74 residue naturally capped or protected by a cysteine, and the six C-terminal residues predicted from the gene encoding the ADA of SEQ ID NO: 5 are not present. However, it is contemplated that the invention can be practiced with alternative variations on natural bovine ADA, including alternative alleles and polymorphisms, both natural and recombinantly produced, with and without the predicted six C-terminal residues. Bovine ADA polymorphisms include, e.g., glutamine at position 198 in place of lysine; alanine at position 245 in place of threonine; arginine at position 351 instead of glycine.

Preferred derivatives of ADA enzyme include recombinantly produced ADA enzyme that has been mutated for enhanced stability relative to nonmutated recombinant ADA enzyme. These include, for example, recombinant ADA enzymes modified from SEQ ID NO: 5 and/or SEQ ID NO: 5 with one or more of the above-noted polymorphisms, to replace an oxidizable Cys residue that is solvent-exposed with a suitable non-oxidizable amino acid residue. Such non-oxidizable residue includes any art-known natural amino acid residue and/or any art-known derivatives thereof. For example, mature recombinant ADA expressed from a gene first isolated from a bovine or human source has an unstable $Cys_{74}$ residue that is preferably replaced with a non-oxidizable amino acid residue, e.g., by a $Ser_{74}$. Such recombinant ADA enzymes are illustrated by SEQ ID NO: 1 (bovine ADA structure) and SEQ ID NO: 3 (human ADA structure). SEQ ID NO: 2 and SEQ ID NO: 4 illustrate useful DNA molecules for expressing the same, that have been codon optimized for *E. coli* expression. Additional details concerning such recombinant ADA muteins, and production and purification of these proteins, are provided by co-owned U.S. patent application Ser. No. 12/105,913, which claims the benefit of priority of U.S. Patent Application No. 60/913,009, entitled "Stable Recombinant Adenosine Deaminase" filed on even date herewith, and incorporated by reference herein in their entirety. Specific details on the vectors and methods of purification are found therein, particularly in the Examples section, and most particularly in Examples 1-4.

Alternatively, ADA enzymes can be stabilized, as needed, by capping a solvent-exposed oxidizable Cys residue, by treating the ADA enzyme with a sufficient amount of a capping agent, under reaction conditions sufficient to cap the reactive cysteine, without substantially inactivating the ADA protein. This process is preferably employed with recombinantly produced ADA, either mutein or wild-type ADA enzymes.

For example, capping agents include, without limitation, oxidized glutathione (preferred), iodoacetamide, iodoacetic acid, cystine, and other dithiols known to those of ordinary skill, and mixtures thereof. The amount and concentration of the capping agent included during the reacting phase of the methods described herein will depend somewhat upon the specific capping agent used and the needs of the artisan but will not be subject to undue experimentation. Using oxidized glutathione as a prototype, the concentration of used when reacted with the recombinant protein such as rhADA can range from about 25 µM to about 100 mM. Preferably, the oxidized glutathione is reacted with the recombinant protein at a concentration of from about 5 nM to about 25 mM.

The reaction conditions employed during the reacting of the capping agent and the recombinant protein further include the use of an aqueous solution having a pH of from about 6.5 to about 8.4, preferably from about 7.2 to about 7.8. In addition, the aqueous solution preferably includes a suitable buffer such as sodium phosphate, potassium phosphate, Tris, and Hepes and mixtures thereof at concentrations ranging from 10 to 150 mM (optionally, capping can take place out of this buffer range, lower than 10 or high than 150 mM). The reaction conditions further include allowing the reaction to proceed at temperatures which will not contribute to degradation of the protein, i.e. from about 4-37° C. Optionally, capping can take place outside of this temperature range, e.g., at a temperature range lower than 0-4° C. or higher than 37° C. The reaction is conducted for a time sufficient to achieve the desired stabilization of the reactive cysteine. Simply by way of example, the reaction is conducted for a time ranging from about 5 seconds to about 8 hours (e.g., overnight).

Additional details regarding capped, stabilized recombinant ADA is provided by co-owned U.S. patent application Ser. No. 11/738,012 entitled "Stabilized Proteins", and particularly in the examples section, that is incorporated herein by reference.

Further, the use of singular terms for convenience in description is in no way intended to be so limiting. Thus, for example, reference to a composition comprising an enzyme refers to one or more molecules of that enzyme. It is also to be understood that this invention is not limited to the particular configurations, process steps, and materials disclosed herein as such configurations, process steps, and materials may vary somewhat.

A. Polymer-ADA Conjugates

A preferred form of ADA is in the form of a polymer conjugated enzyme. The ADA-polymer conjugates of the present invention generally correspond to formula (I):

$$[R-NH]_z-(ADA) \qquad (I)$$

wherein (ADA) represents the adenosine deaminase enzyme or optionally, a derivative or fragment thereof;

NH— is an amino group of an amino acid found on the ADA, derivative or fragment thereof for attachment to the polymer;

(z) is a positive integer, preferably from about 1 to about 80, more preferably from about 5 to about 80, yet more preferably from about 11 to about 18; and R is a substantially non-antigenic polymer residue that is attached to the ADA in a releasable or non-releasable form.

The non-antigenic polymer residue portion of the conjugate (R) can be selected from among a non-limiting list of polymer-based systems such as:

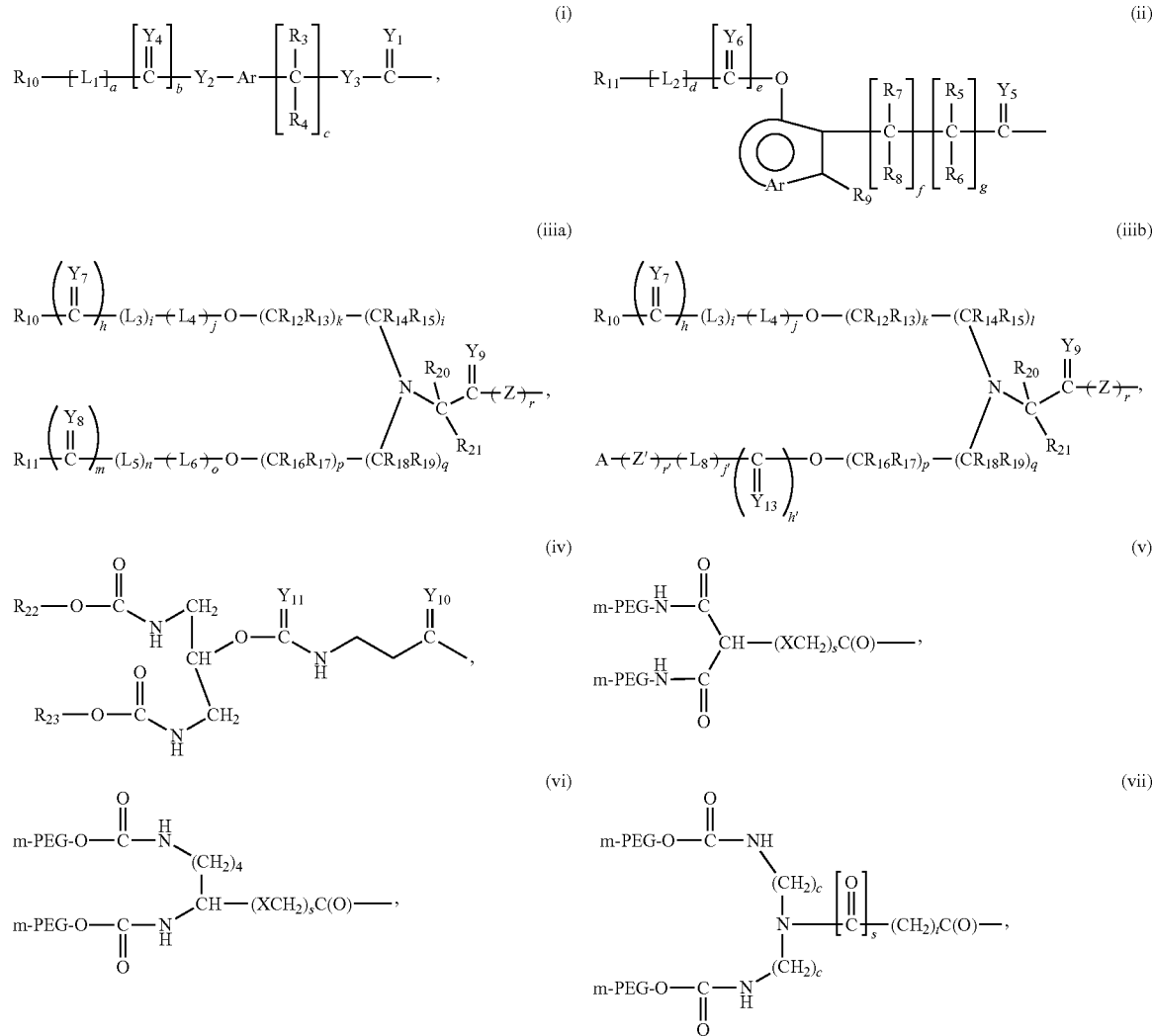

-continued

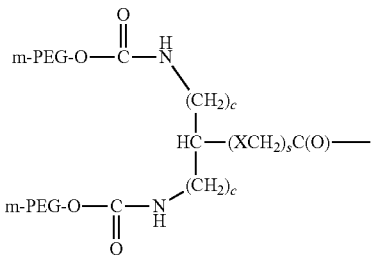
(viii)

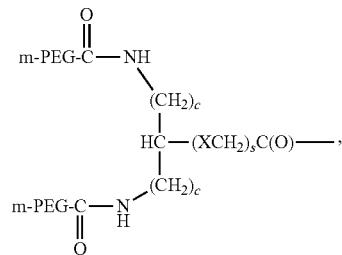
(ix)

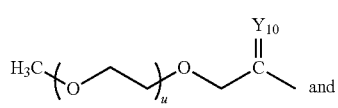
and
(x)

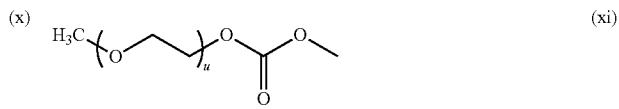
(xi)

wherein:

$R_{10-11}$, and $R_{22-23}$ may be the same or different and are independently selected non-antigenic polymer residues;

$R_{3-9}$, $R_{12-21}$ and $R_{24}$ (see below) are the same or different and are each independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxys;

Ar is a moiety which forms a multi-substituted aromatic hydrocarbon or a multi-substituted heterocyclic group;

mPEG is methoxy PEG and (u) is a positive integer to provide polymers having a total molecular weight of from about 2,000 to about 100,000 Da, preferably from about 4,000 to about 45,000 Da/

Within the above, it is preferred that $Y_{1-11}$ and $Y_{13}$ are O; $R_{3-8}$, $R_{12-21}$ and $R_{24}$ are each independently either hydrogen or $C_{1-6}$ alkyls, with methyl and ethyl being the most preferred alkyls and $R_{7-9}$ are preferably $CH_3$.

In a further aspect of the invention, the polymer portion of the conjugate can be one which affords multiple points of attachment for the ADA. A non-limiting list of such systems include:

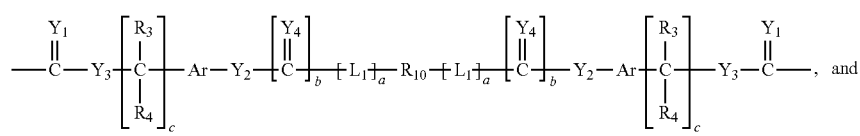
(xii)

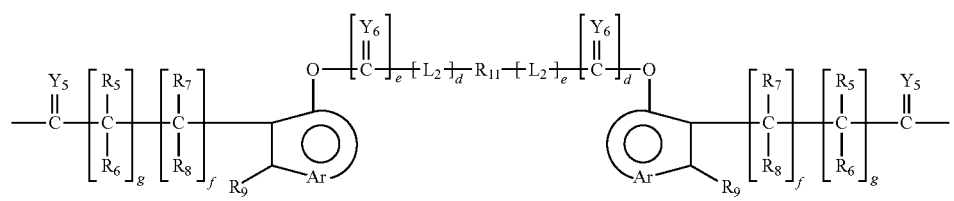
(xiii)

$Y_{1-11}$ and $Y_{13}$ may be the same or different and are independently selected from O, S and $NR_{24}$;

A is selected from among alkyl groups, targeting moieties, diagnostic agents, and biologically active moieties;

X is O, NQ, S, SO or $SO_2$; where Q is H, $C_{1-8}$ alkyl, $C_{1-8}$ branched alkyl, $C_{1-8}$ substituted alkyl, aryl or aralkyl;

Z and Z' are independently selected from among moieties actively transported into a target cell, hydrophobic moieties, bifunctional linking moieties and combinations thereof;

$L_{1-6}$ and $L_8$ may be the same or different and are independently selected bifunctional linker groups;

(a), (c), (d), (f), (g), (i), (k), (l), (n), (o), (p), (q) and (t) may be the same or different and are independently 0 or a positive integer, preferably, in most aspects; (b), (e), (r), (r'), (s), (h), (h') and (m) may be the same or different and are independently 0 or 1;

wherein all variables are the same as that set forth above.

Alternatively and/or preferably, multiple PEG strands are attached to the ADA. In these aspects, the ADA polymer conjugates can include at least 5 polyethylene glycol strands up to 80 strands attached to epsilon amino groups of Lys on the enzyme, but preferably, can include about 11-18 PEG strands attached to epsilon amino groups of Lys on the enzyme.

While the ADA is conjugated to from about 11 to about 18 PEG molecules per enzyme molecule, via lysine linkages, the ratio of PEG to ADA can be varied in order to modify the physical and kinetic properties of the combined conjugate to fit any particular clinical situation.

The activated polymers which can be employed to make the ADA conjugates will naturally correspond directly with the polymer portions described above. The chief difference is the presence of a leaving or activating group, sometimes designated herein as $B_1$, which facilitates the attachment of the polymer system to an amine group (e.g., epsilone amine group of lysine) found on the ADA. Thus, compounds (i)-(xiii) include a leaving or activating group such as:

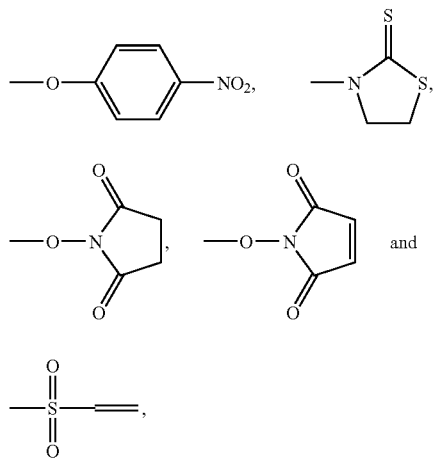

or other suitable leaving or activating groups such as N-hydroxybenzotriazolyl, halogen, N-hydroxyphthalimidyl, imidazolyl, O-acyl ureas, pentafluorophenol or 2,4,6-tri-chlorophenol or other suitable leaving groups apparent to those of ordinary skill, found in the place where the ADA attaches after the conjugation reaction.

Some preferred activated PEGs include those disclosed in commonly assigned U.S. Pat. Nos. 5,122,614, 5,324,844, 5,612,460 and 5,808,096 (succinimidyl carbonate-activated polyethylene glycol (SC-PEG) and related activated PEG's), and U.S. Pat. No. 5,349,001 (cyclic imide thione activated PEG's), the contents of which are incorporated herein by reference. As will be appreciated by those of ordinary skill such conjugation reactions typically are carried out in a suitable buffer using a several-fold molar excess of activated PEG. Some preferred conjugates made with linear PEGs like the above mentioned SC-PEG can contain, on average, from about 1 to about 80 PEG strands per enzyme. Consequently, for these, molar excesses of several hundred fold, e.g., 200-1000× can be employed. The molar excess used for branched polymers and polymers attached to the enzyme will be lower and can be determined using the techniques described in the patents and patent applications describing the same that are mentioned herein below.

For purposes of the present invention, activated groups are to be understood as those groups which are capable of reacting with an amine group (nucleophile) found on an ADA, e.g. on a Lys.

For purposes of the present invention, the foregoing are also referred to as activated polymer linkers. The polymer residues are preferably polyalkylene oxide-based and more preferably polyethylene glycol (PEG) based wherein the PEG is linear, branched or multi-armed.

Referring now to the polymers described above, it can be seen that the Ar is a moiety which forms a multi-substituted aromatic hydrocarbon or a multi-substituted heterocyclic group. A key feature is that the Ar moiety is aromatic in nature. Generally, to be aromatic, the pi electrons must be shared within a "cloud" both above and below the plane of a cyclic molecule. Furthermore, the number of pi electrons must satisfy the Huckle rule (4n+2). Those of ordinary skill will realize that a myriad of moieties will satisfy the aromatic requirement of the moiety and thus are suitable for use herein.

In some preferred aspects of the invention, the activated polymer linkers of the polymeric systems based on benzyl elimination or trimethyl lock lactonization are prepared in accordance with commonly-assigned U.S. Pat. Nos. 6,180, 095, 6,720,306, 5,965,119, 6,624,142 and 6,303,569, the contents of which are incorporated herein by reference. Within this context, the following activated polymer linkers are preferred:

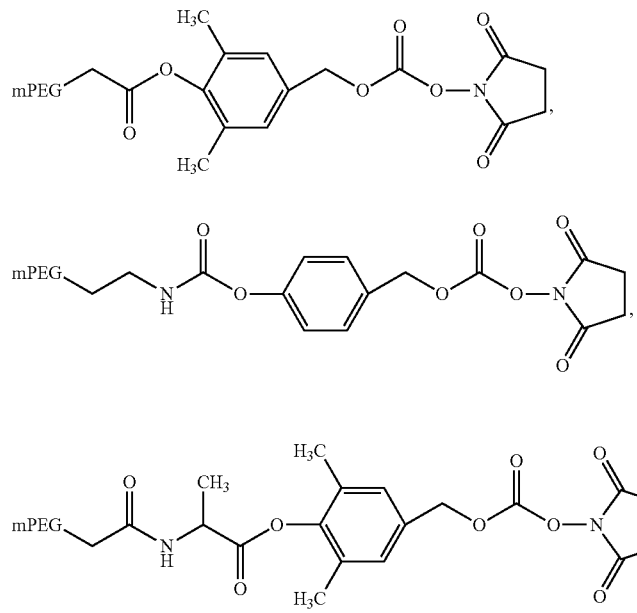

-continued
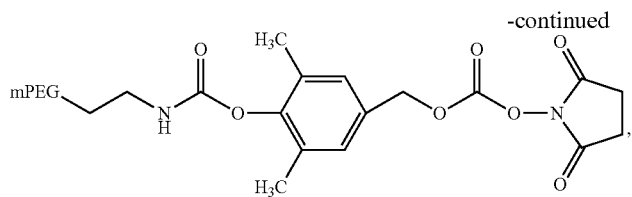
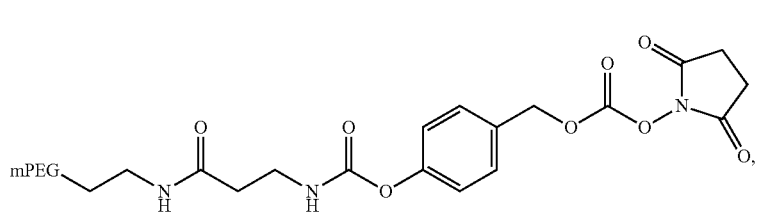
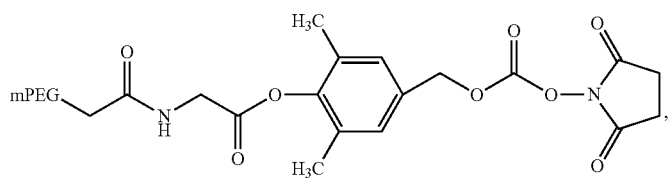
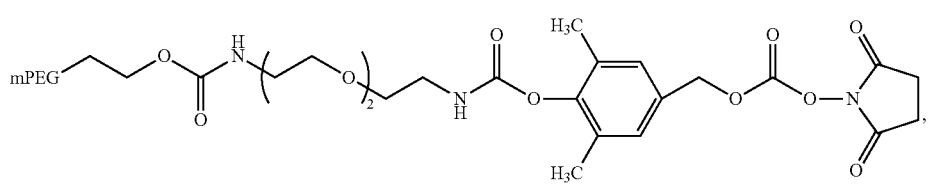
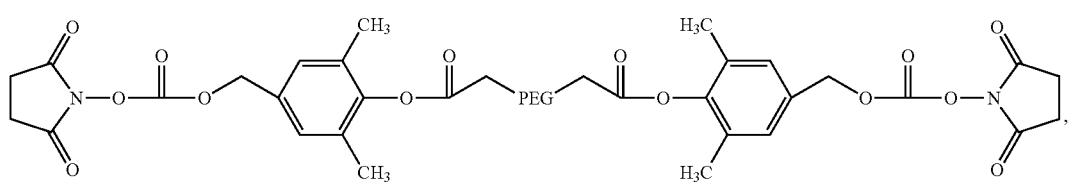
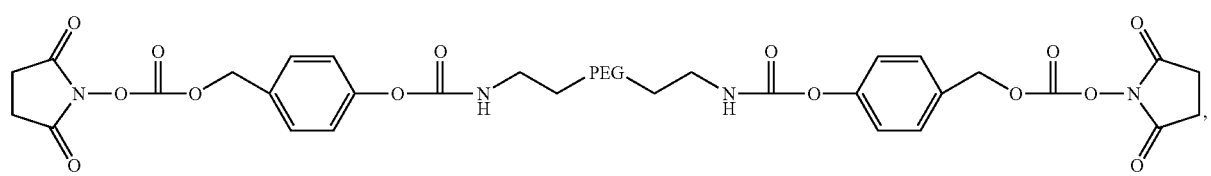
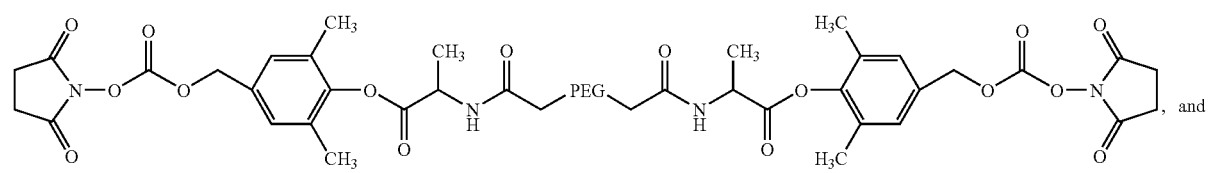, and
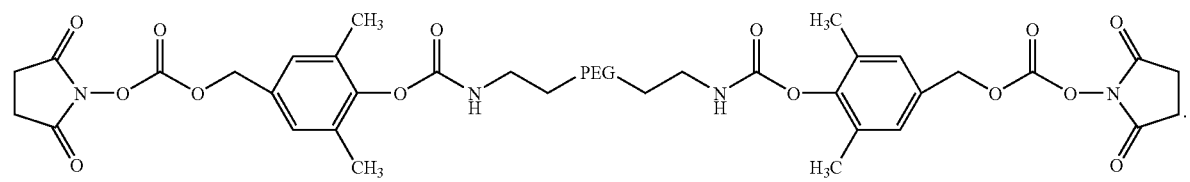.
In one alternative aspect of the invention, the ADA polymer conjugates are made using certain bicine polymer residues such as those described in commonly assigned U.S. Pat. Nos. 7,122,189 and 7,087,229 and U.S. patent application Ser. Nos. 10/557,522, 11/502,108, and 11/011,818. The disclosure of each such patent application is incorporated herein by reference. A few of the preferred activated polymers include:

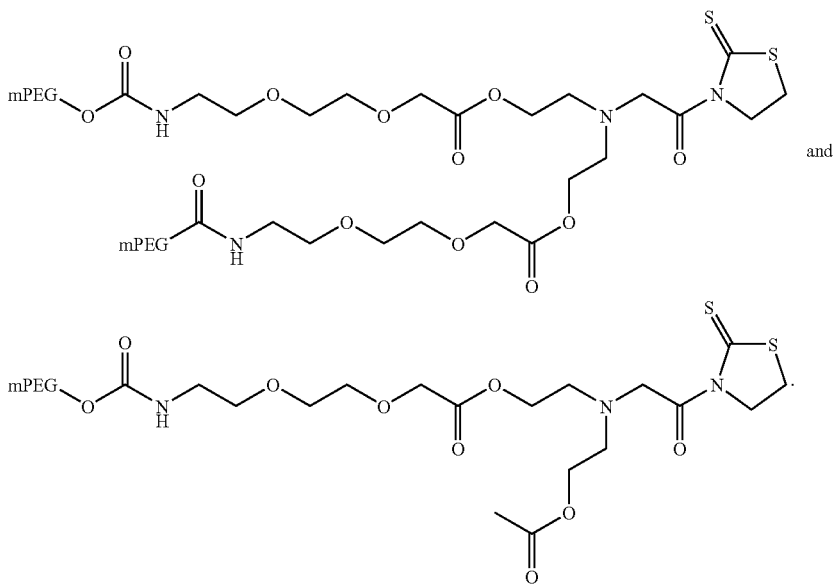

It should also be understood that the leaving or activating group shown above is only one of the suitable groups and the others mentioned herein can also be used without undue experimentation.

In alternative aspects, the activated polymer linkers are prepared using branched polymer residues such as those described commonly assigned U.S. Pat. Nos. 5,681,567, 5,756,593, 5,643,575; 5,919,455, 6,113,906, 6,153,655, 6,395,266 and 6,638,499, 6,251,382 and 6,824,766, the disclosure of each being incorporated herein by reference. Such activated polymers correspond to polymer systems (iv)-(ix) with the following being representative:

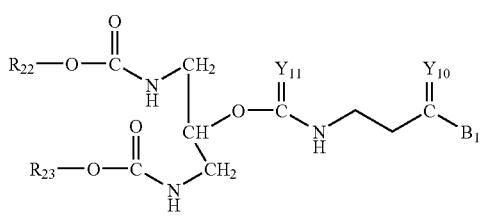

wherein $B_1$ is an activating group and all variables are as previously defined.

In yet alternative aspects, the activated polymers can employ a hindered ester-based linker. See PCT/US07/78593 entitled "Polyalkylene Oxides Having Hindered Ester-Based Biodegradable Linkers", the content of which are incorporated by reference. For example, a non-limiting list of such compounds includes:

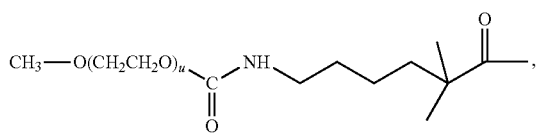

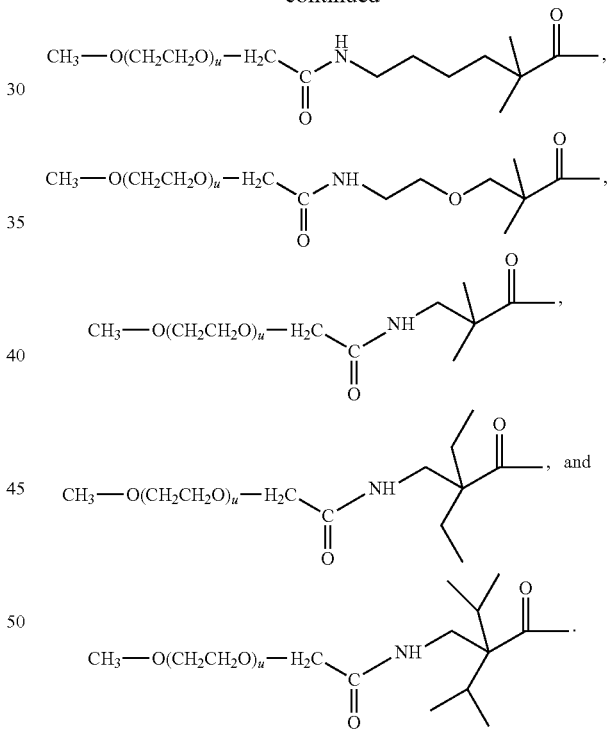

wherein (u) is an integer ranging from about 10 to about 2300, to preferably provide polymers having a total molecular weight of from about 4,000 to about 45,000.

In one preferred embodiment, the activated polyethylene glycol is one which provides a urethane linkage or amide-linkage with the protein.

Methods of preparing polymers having terminal carboxylic acids in high purity are described in U.S. patent application Ser. No. 11/328,662, the contents of which are incorporated herein by reference. The methods include first preparing a tertiary alkyl ester of a polyalkylene oxide followed by conversion to the carboxylic acid derivative thereof. The first step of the preparation of the PAO carboxylic acids of the process includes forming an intermediate such as t-butyl ester of polyalkylene oxide carboxylic acid. This intermediate is formed by reacting a PAO with a t-butyl haloacetate in the presence of a base such as potassium t-butoxide. Once the t-butyl ester intermediate has been formed, the carboxylic acid derivative of the polyalkylene oxide can be readily provided in purities exceeding 92%, preferably exceeding 97%, more preferably exceeding 99% and most preferably exceeding 99.5% purity.

In yet alternative aspects, polymers having terminal amine groups can be employed to make the ADA conjugates. The methods of preparing polymers containing terminal amines in high purity are described in U.S. patent application Ser. Nos. 11/508,507 and 11/537,172, the contents of each of which are incorporated by reference. For example, polymers having azides react with phosphine-based reducing agent such as triphenylphosphine or an alkali metal borohydride reducing agent such as $NaBH_4$. Alternatively, polymers including leaving groups react with protected amine salts such as potassium salt of methyl-tert-butyl imidodicarbonate (KNMeBoc) or the potassium salt of di-tert-butyl imidodicarbonate ($KNBoc_2$) followed by deprotecting the protected amine group. The purity of the polymers containing the terminal amines formed by these processes is greater than about 95% and preferably greater than 99%.

1. Substantially Non-Antigenic Polymers

As stated above, $R_{10-11}$, and $R_{22-23}$ are preferably each water soluble polymer residues which are preferably substantially non-antigenic such as polyalkylene oxides (PAO's) and more preferably polyethylene glycols such as mPEG. For purposes of illustration and not limitation, the polyethylene glycol (PEG) residue portion of $R_{10-11}$, and $R_{22-23}$ can be selected from among:

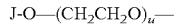

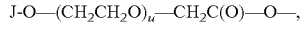

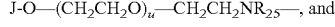

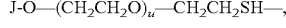

wherein:

(u) is the degree of polymerization, i.e. from about 10 to about 2,300;

$R_{25}$ is selected from among hydrogen, $C_{1-6}$ alkyls, $C_{2-6}$ alkenyls, $C_{2-6}$ alkynyls, $C_{3-12}$ branched alkyls, $C_{3-8}$ cycloalkyls, $C_{1-6}$ substituted alkyls, $C_{2-6}$ substituted alkenyls, $C_{2-6}$ substituted alkynyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, and J is a capping group, i.e., a group which is found on the terminal of the polymer and, in some aspects, can be selected from any of $NH_2$ (or $CH_2CH_2NH_2$), H, SH (or $CH_2CH_2SH$), $CO_2H$ (or $CH_2CO_2H$), $C_{1-6}$ alkyls, preferably methyl, or other PEG terminal activating groups, as such groups are understood by those of ordinary skill.

In one particularly preferred embodiment, $R_{10-11}$, and $R_{22-23}$ are selected from among,

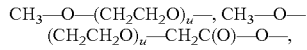

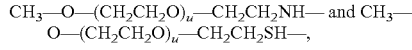

where (u) is a positive integer, preferably selected so that the average total molecular weight of the polymer portion ranges from about 2,000 to about 100,000 Da. More preferably, $R_{10-11}$, and $R_{22-23}$ independently have an average total molecular weight of from about 4,000 Da to about 4,5000 Da, with a weight average molecular weight of from about 5,000 Da being most preferred. Other molecular weights are also contemplated so as to accommodate the needs of the artisan.

PEG is generally represented by the structure:

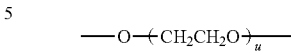

and $R_{10-11}$, and $R_{22-23}$ preferably comprise residues of this formula. The degree of polymerization for the polymer represents the number of repeating units in the polymer chain and is dependent on the molecular weight of the polymer.

Alternatively, the polyethylene glycol (PEG) residue portion of the invention can be represented by the structure:

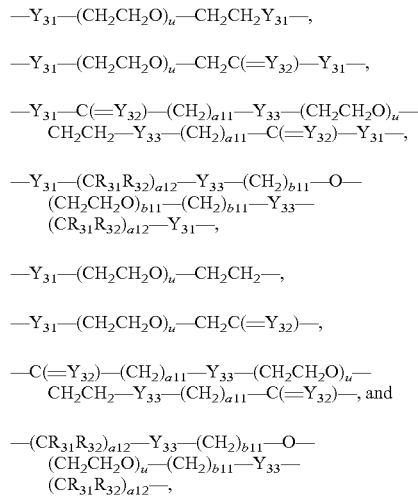

wherein:

$Y_{31}$ and $Y_{33}$ are independently O, S, SO, $SO_2$, $NR_{33}$ or a bond;

$Y_{32}$ is O, S, or $NR_{34}$;

$R_{31-34}$ are independently selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy;

(a11), (a12), and (b11) are independently zero or a positive integer, preferably 0-6, and more preferably 0, 1 or 2; and (u) is an integer from about 10 to about 2300.

As an example, the PEG can be functionalized in the following non-limiting manner:

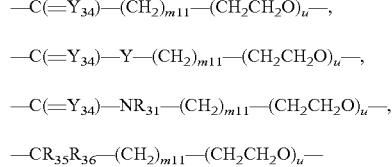

wherein $R_{31}$, $R_{35}$ and $R_{36}$ are independently selected from among H, $C_{1-6}$ alkyls, aryls, substituted aryls, aralkyls, heteroalkyls, substituted heteroalkyls and substituted $C_{1-6}$ alkyls;

(m11) is zero or is a positive integer, and preferably 1 or 2;

$Y_{34}$ is O or S; and (u) represents the degree of polymerization.

In these aspects, a capping group (J) such as methyl is attached to the terminal of the PEG.

For example, the conjugates of the present invention can be made by methods which include converting the multi-arm PEG-OH or "star-PEG" products such as those described in NOF Corp. Drug Delivery System catalog, Ver. 8, April 2006, the disclosure of which is incorporated herein by reference, into a suitably activated polymer, using the activation techniques described in the aforementioned U.S. Pat. Nos. 5,122,614 or 5,808,096. See also Shearwater Corporation's 2001 catalog "Polyethylene Glycol and Derivatives for Biomedical Application", incorporated herein by reference.

The multi-arm polymers contain four or more polymer arms and preferably four or eight polymer arms. For purposes of illustration and not limitation, the multi-arm polyethylene glycol (PEG) residue can be of the formula:

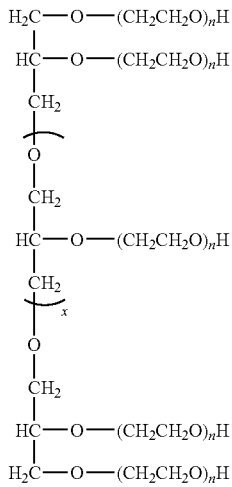

wherein:

(x) is 0 and a positive integer, i.e. from about 0 to about 28; and (n) is the degree of polymerization.

In one particular embodiment of the present invention, the multi-arm PEG has the structure:

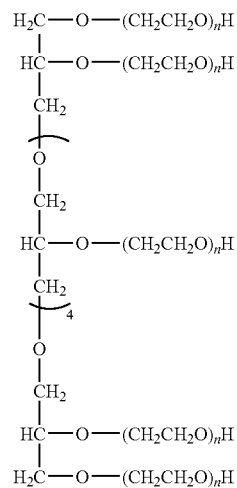

wherein (n) is a positive integer. In one preferred embodiment of the invention, the polymers have a total molecular weight of from about 2,000 Da to about 100,000 Da, and preferably from 4,000 Da to 45,000 Da.

Specifically, the PEG can be of the formula:

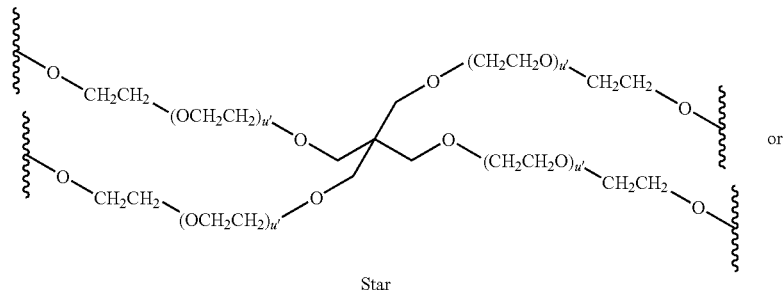

Star or

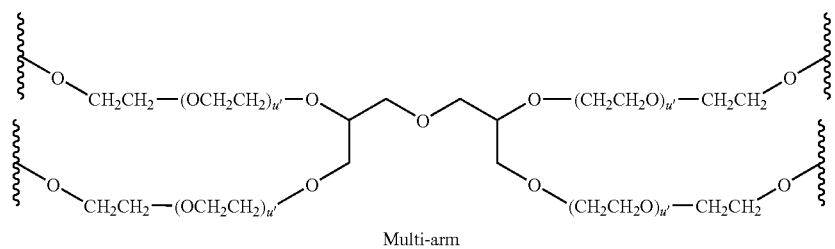

Multi-arm wherein:

(u') is an integer from about 10 to about 570, to preferably provide polymers having a total molecular weight of from about 4,000 to about 45,000; and up to 3 terminal portions of the residue is/are capped with a methyl or other lower alkyl.

In some preferred embodiments, all 4 of the PEG arms are converted to suitable functional groups, i.e. SC, etc., for facilitating attachment to the recombinant protein. Such compounds prior to conversion include:

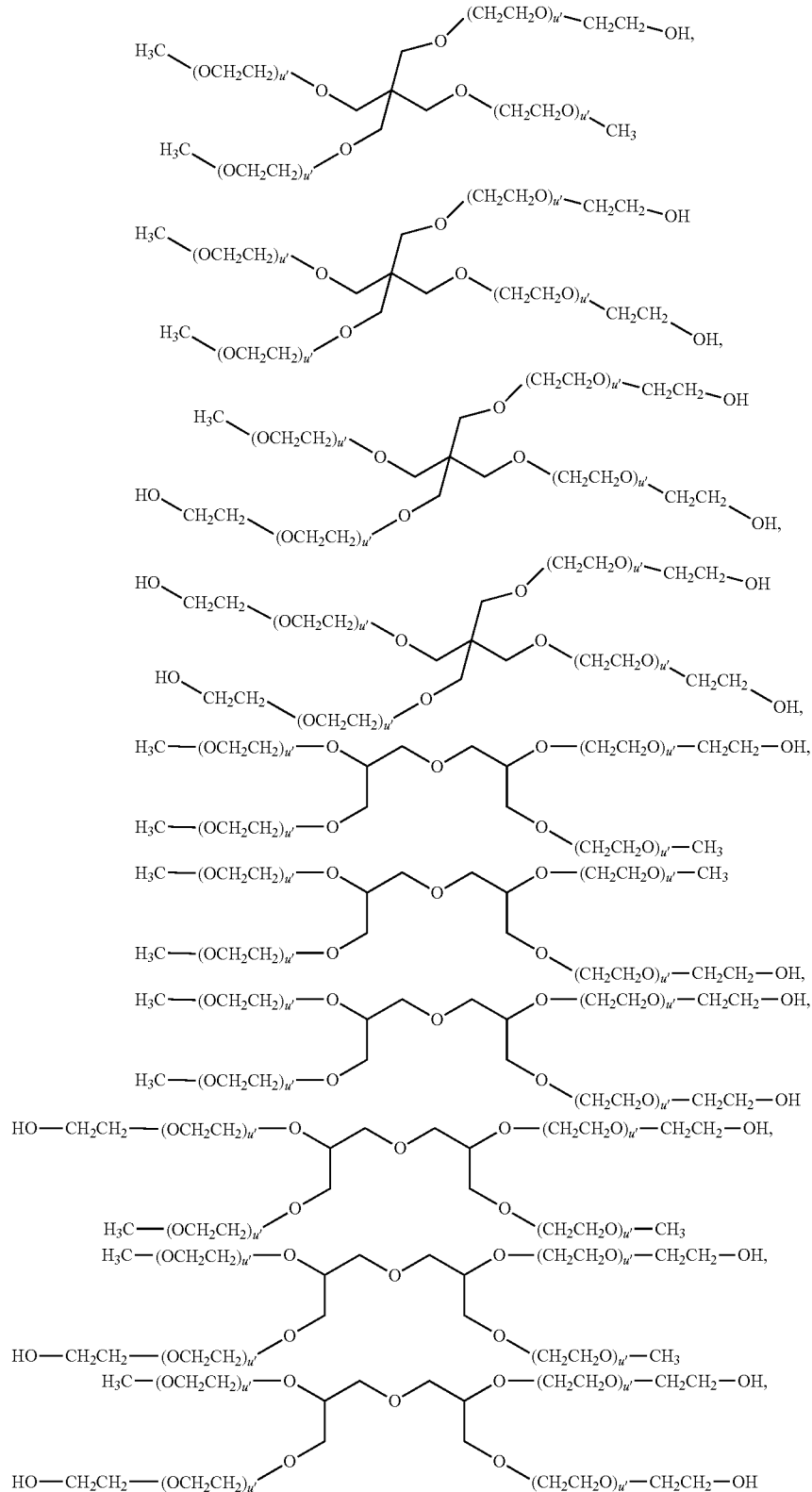

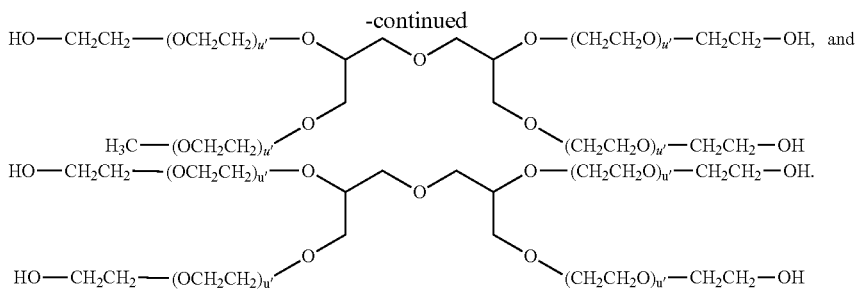

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO-based polymers, $R_{10-11}$, and $R_{22-23}$ are each optionally selected from among one or more effectively non-antigenic materials such as dextran, polyvinyl alcohols, carbohydrate-based polymers, hydroxypropylmeth-acrylamide (HPMA), polyalkylene oxides, and/or copolymers thereof. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated and that other polyalkylene oxide derivatives such as the polypropylene glycols, etc. are also contemplated.

2. Bifunctional Linker Groups

In many aspects of the invention, $L_{1-6}$ and $L_8$ are linking groups which facilitate attachment of the polymer strands, e.g. $R_{10-11}$, and/or $R_{22-23}$. The linkage provided can be either direct or through further coupling groups known to those of ordinary skill. In this aspect of the invention, $L_{1-6}$ and $L_8$ may be the same or different and can be selected from a wide variety of groups well known to those of ordinary skill such as bifunctional and heterobifunctional aliphatic and aromatic-aliphatic groups, amino acids, etc. Thus, $L_{1-6}$ and $L_8$ can be the same or different and include groups such as:

—NH(CH$_2$CH$_2$)$_2$O—,

—NH(CH$_2$CH$_2$)(CH$_2$CH$_2$O)NH—,

—O(CH$_2$CH$_2$)NH—,   —O(CH$_2$CH$_2$)O—,

—NH(CH$_2$CH$_2$)NH—,   —NH(CH$_2$CH$_2$)(CH$_2$CH$_2$O)—,

—NH(CH$_2$CH$_2$O)—,   —NH(CH$_2$CH$_2$O)(CH$_2$)NH—,

—NH(CH$_2$CH$_2$O)$_2$—,   —O(CH$_2$)$_3$NH—,

—O(CH$_2$)$_3$O—,   —O(CH$_2$CH$_2$O)$_2$NH—,

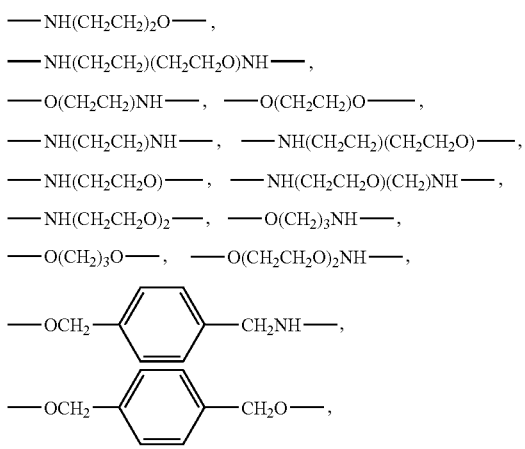

Preferably, $L_{1-6}$ and $L_8$ are selected from among:

—C(O)CH$_2$OCH$_2$C(O)—;

—C(O)CH$_2$NHCH$_2$C(O)—;

—C(O)CH$_2$SCH$_2$C(O)—;

—C(O)CH$_2$CH$_2$CH$_2$C(O)—, and

—C(O)CH$_2$CH$_2$C(O)—.

Alternatively, suitable amino acid residues can be selected from ally of the known naturally-occurring L-amino acids, e.g., alanine, valine, leucine, etc. and/or a combination thereof, to name but a few. $L_{1-6}$ and $L_8$ can also include a peptide which ranges in size, for instance, from about 2 to about 10 amino acid residues.

Derivatives and analogs of the naturally occurring amino acids, as well as various art-known non-naturally occurring amino acids (D or L), hydrophobic or non-hydrophobic, are also contemplated to be within the scope of the invention.

3. Z Moieties and their Function

In one aspect of the invention, Z and Z' are $L_7$-C(=$Y_{12}$) wherein $L_7$ is a bifunctional linker selected from among the group which defines $L_{1-6}$, and $Y_{12}$ is selected from among the same groups as that which defines $Y_1$. In this aspect of the invention, the Z group selves as the linkage between the ADA and the remainder of the polymer delivery system. In other aspects of the invention, Z is a moiety that is actively transported into a target cell, a hydrophobic moiety, and combinations thereof. The Z' when present can serve as a bifunctional linker, a moiety that is actively transported into a target cell, a hydrophobic moiety, and combinations thereof.

In this aspect of the invention, the releasable polymer systems are prepared so that in vivo hydrolysis cleaves the polymer from the ADA and releases the enzyme into the extracellular fluid, while still linked to the Z moiety. For example, some potential Z-B combinations are leucine-ADA and Gly-Phe-Leu-Gly-ADA.

B. Preparation of ADA Conjugates

For purposes of illustration, suitable conjugation reactions include reacting ADA with a suitably activated polymer system described herein. The reaction is preferably carried out using conditions well known to those of ordinary skill for protein modification, including the use of a PBS buffered system, etc. with the pH in the range of about 6.5-8.5. It is contemplated that in most instances, an excess of the activated polymer will be reacted with the ADA.

Reactions of this sort will often result in the formation of conjugates containing one or more polymers attached to the ADA. As will be appreciated, it will often be desirable to isolate the various fractions and to provide a more homogenous product. In most aspects of the invention, the reaction mixture is collected, loaded onto a suitable column resin and the desired fractions are sequentially eluted off with increasing levels of buffer. Fractions are analyzed by suitable analytical tools to determine the purity of the conjugated protein before being processed further. Regardless of the synthesis route and activated polymer selected, the conjugates will conform to Formula (I) as defined herein. Some of the preferred conjugates which result from the synthetic techniques described herein include:

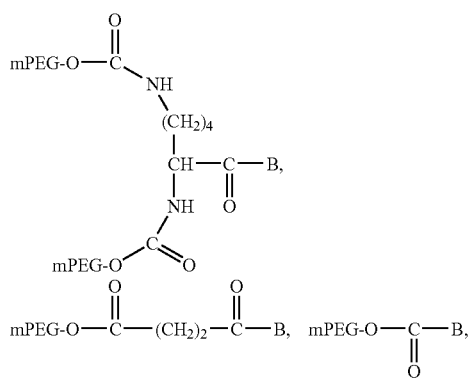

wherein B is ADA.

Still further conjugates made in accordance with the present invention include:

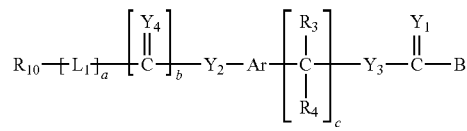

wherein all variables are the same as that set forth above and B is ADA.

Further conjugates include:

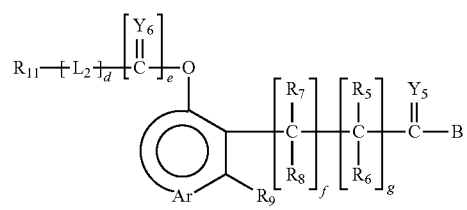

wherein B is ADA.

A particularly preferred conjugate is:

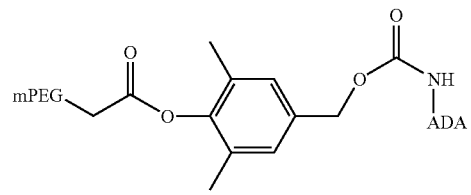

wherein the molecular weight of the mPEG is from about 4,000 to about 45,000.

When the bicine-based polymer systems are used, two preferred conjugates are:

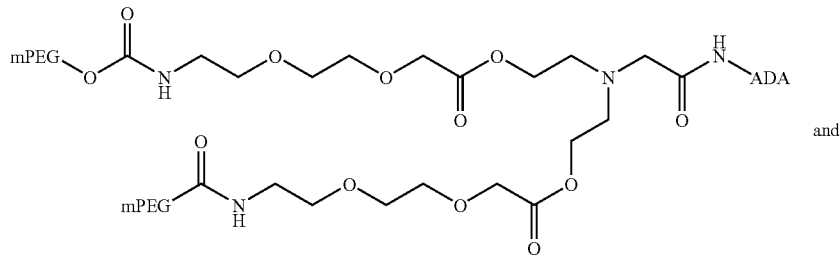

and

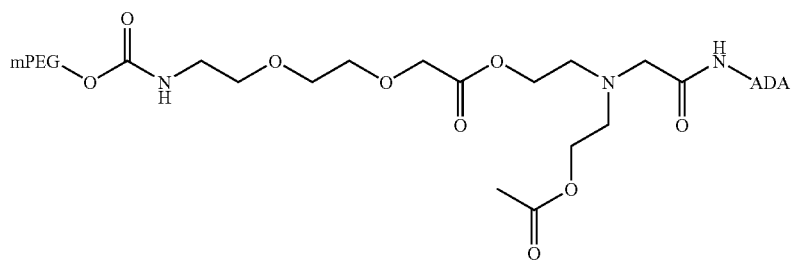

wherein the molecular weights of the mPEG are the same as above.

More preferred conjugates include

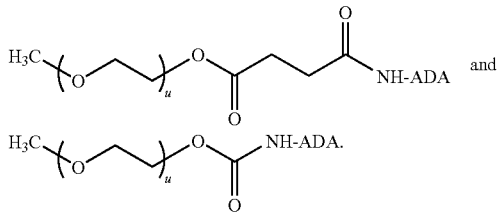

It is noted that PEGylation of ADA will be empirically optimized for total PEG attachments per protein, PEG polymer size, and PEG linker design. Key characteristics of the PEGylated ADA for evaluation of PEGylation optimization include both in vitro assays (e.g., enzyme activity and stability) and in vivo assays (e.g. pharmacokinetics and pharmacodynamics).

C. Tumors to be Treated

The inventive methods are applicable to treating all types of tumors, including cancers, that are susceptible to a reduction in adenosine or deoxyadenosine levels in the blood and/or tissues of a human or animal to be treated. Broadly, these include tumors of the blood as well as solid tumors. Among solid tumors are included those that are suppressed when reduced levels of adenosine allow the patient immune system to more effectively suppress the tumor and/or tumors that are suppressed when reduced levels of adenosine inhibit the blood supply, e.g., in already hypoxic tumors.

More preferably, tumors susceptible to treatment by the inventive methods are solid tumors, which benefit from the additional effect of a reduction in angiogenic stimulation, that accompanies a reduction in tissue levels of adenosine.

Tumors to be treated include, simply by way of example, those that originate in the immune system, skeletal system, muscles and heart, breast, gastrointestinal tract, central and peripheral nervous system, renal system, reproductive system, respiratory system, skin, connective tissue systems, including joints, fatty tissues, circulatory system, including blood vessel walls, and the like.

Tumors of the skeletal system include, e.g., both sarcomas and blastomas such as osteosarcoma, chondrosarcoma, chondroblastoma, etc. Muscle and heat tumors include tumors of both skeletal and smooth muscles, e.g., leiomyomas (benign tumors of smooth muscle), leiomyosarcomas, rhabdomyomas (benign tumors of skeletal muscle), rhabdomyosarcomas, cardiac sarcoma, etc. Tumors of the gastrointestinal tract include e.g., tumors of the mouth, esophagus, stomach, small intestine, colon and colorectal tumors, as well as tumors of gastrointestinal secretory organs such as salivary glands, liver, pancreas, the biliary tract and the like.

Tumors of the central nervous system include tumors of the brain, retina, and spinal cord, and can also originate in associated connective tissue, bone, blood vessels or nervous tissue. Tumors of the peripheral nervous system are also contemplated to be treated. In addition, tumors of the peripheral nervous system include malignant peripheral nerve sheath tumors.

Tumors of the renal system include those of the kidneys, e.g., renal cell carcinoma, as well as tumors of the ureters and bladder. Tumors of the reproductive system include tumors of the cervix, uterus, ovary, prostate, testes and related secretory glands. Tumors of the immune system include both blood based and solid tumors, including lymphomas, e.g., both Hodgkin's and non-Hodgkin's.

Tumors of the respiratory system include tumors of the nasal passages, bronchi and lungs. Tumors of the breast include, e.g., both lobular and ductal carcinoma.

Particularly common types of malignant tumors to be treated include, simply by way of example: prostate cancer, lung cancer, breast cancer, colorectal cancer, bladder cancer, pancreatic cancer, endometrial cancer, ovarian cancer, cutaneous melanoma, lymphomas, non-Hodgkin lymphoma, pancreatic cancer, neuroblastoma, Wilms' tumor, rhabdomyosarcoma (arising from muscle), retinoblastoma, osteosarcoma and Ewing's sarcoma, to name but a few.

D. Dose Selection

The artisan will appreciate that, in a clinical setting, the dosage of Adagen® is individualized depending upon the clinical response of the tumor and the side effect profile of an individual patient, whether animal or human. In the example study provided herein below, the highest dose is the maximum feasible dose that is tolerated. Adagen® is commercially supplied as 250 U/mL. This translates to 2000 U/kg for an approximate 25 g mouse injected with 0.2 ml of Adagen®. The lowest dose employed in the examples studies provided hereinbelow approximates the clinical human dose. The recommended dosing schedule in treating human SCID patients is 10 U/kg for the first dose, 15 U/kg for the second dose, and 20 U/kg for the third dose. Further increases of 5 U/kg/week are permitted, up to a maximum single dose of 30 U/kg. The dose in the below exemplified protocol (100 U/kg) is the mouse equivalent dose of approximately 12 U/kg clinical child dose.

The dose based on the amount of enzyme will range from, for example, about 0.10 U/kg through about 30 U/kg, or higher, preferably from about 0.5 U/kg through about 20 U/kg, and more preferably from about 0.5 U/kg through about 12 U/kg (i.e. per kg of patient body weight) such as from about 0.5 U/kg through about 5 U/kg. A total weekly dose can be up to 40 U/kg, or more, as tolerated by the recipient. Further increases of 5 U/kg/week are permitted, up to a maximum single dose of 30 U/kg, or more, as tolerated by the recipient. In general, following weekly injections of ADAGEN® at 15 U/kg, the average trough level of ADA activity in plasma is between 20 and 25 µmol/hr/mL.

Of course, the artisan will appreciate that the dose of polymer-conjugated ADA can also be adjusted for the particular polymer size, linker chemistry, and valency. For example, the dosing regimen for a polymer conjugate comprising two or four ADA enzymes per polymer will be adjusted according to the units of ADA per ml of solution of any particular polymer conjugate of ADA.

In providing the ADA or ADA PEG-conjugate by injection, the optimal dose range can be adjusted by monitoring adenosine levels in plasma. It is generally desirable to provide the recipient with a dosage that will maintain plasma ADA activity (trough levels) in the range of from about 10 to 100 µmol/hr/mL, preferably from about 15 to about 35 µmol/hr/mL (assayed at 37° C.); and demonstrate a decline in erythrocyte adenosine, i.e., dATP to ≤about 0.001-0.057 µmol/mL, preferably about 0.005-about 0.015 µmol/mL in packed erythrocytes, or ≤about 1% of the total erythrocyte adenosine (i.e., ATP+dATP content), with a normal adenosine level, as measured in a pre-injection sample. The normal value of dATP is below about 0.001 µmol/mL.

Details of ADA dosage information are described in the prescription insert for ADAGEN® (Enzon, Inc.), the contents of which are incorporated herein.

EXAMPLES

The following examples serve to provide further appreciation of the invention but are not meant in any way to restrict the effective scope of the invention.

Example 1

Antitumor Efficacy of Adagen® in DU145 Human Prostate Tumor Xenograft Model

A) Test System

| | |
|---|---|
| Species: | Mouse, *Mus musculus* |
| Strain: | Athymic nude |
| Supplier: | Harlan-Sprague Dawley |
| Sex: | Female |
| Mean Initial Weight: | 27.2 g |
| No. on Study: | 40 |
| Acclimation Period: | 7 days following arrival |
| Identification: | Cage number and ear punch |

B) Methods
Experimental Design:

DU 145 human prostate cancer cells were obtained from the American Type Culture Collection (ATTC), Manassas, Va. Tumors were established in nude mice by subcutaneous injection of $2.0 \times 10^6$ DU 145 cells/mouse into the right axillary flank. Tumor growth was monitored twice weekly and measured once palpable. When tumors reached an average volume of 78 mm³, mice were divided into experimental groups (8/group). Mice were treated with Adagen® at either 2000, 500, or 100 IU/kg twice weekly for 5 weeks. As a positive control, mice received Avastin® (Bevacizumab, an anti-VEGF monoclonal antibody) at 5 mg/kg dose at the same frequency as Adagen®. The experimental groups were set up as shown in Table 1, below. The first day of dosing was designated as Day 1. The tumor volume for each mouse was determined by measuring two dimensions with calipers and calculated using the formula: tumor volume=(length×width²)/2). Mouse weight and tumor size were measured at the beginning of the study and twice weekly throughout the 8-week period.

TABLE 1

| Group # | Group | # animals (n) | Dose (IU/kg) | Route of injection | Dosing schedule |
|---|---|---|---|---|---|
| 1 | Control | 8 | Saline | i.p. | Twice Weekly × 5 |
| 2 | Adagen ® | 8 | 2000 | i.p. | Twice Weekly × 5 |
| 3 | Adagen ® | 8 | 500 | i.p. | Twice Weekly × 5 |
| 4 | Adagen ® | 8 | 100 | i.p. | Twice Weekly × 5 |
| 5 | Avastin ® | 8 | 5 mg/kg | i.p. | Twice Weekly × 5 |

Dose Selection:
Adagen ® or Avastin ® was administered by the intraperitoneal ("i.p.") route twice weekly for five weeks (total: 10 doses).
Adagen ®: Lot Number: NV0604, Concentration: 229 IU/ml
Avastin ®: Lot Number: M66781, Concentration: 25 mg/ml
Dose Calculations were based on body weight taken on day 1.

Clinical Examinations:

The mice were examined visually upon arrival. Thereafter, mice were individually examined twice a week following initial tumor palpation, for clinical signs, general behavioral changes, and monitored for body weight. Any death and clinical sign were recorded. Food and water consumption was not monitored. Mice bearing tumors that showed open necrotic lesions were sacrificed. Mice losing more than 20% of body weight were also humanely sacrificed.

Statistical Analysis:

Differences in % change in tumor volume between various treatments were compared using one way analysis of variance. All pairwise multiple comparisons were made using the Holm-Sidak method.

C) Results
Definitions of the Terms Used:
(a) % of Initial tumor volume: (Tumor volume on any given day/Tumor volume on Day 1)×100
(b) % change in tumor volume: [(Tumor volume on any given day-Tumor volume on Day 1)/Tumor volume on day 1]×100
(c) % Tumor growth inhibition (TGI): [(Mean tumor volume of control group-Mean tumor volume of treatment group)/Mean tumor volume of control group]×100
(d) Regression of tumor is defined as negative tumor volume compared to day 1
(e) Cure is defined as complete absence of tumor as observed from naked human eye.

The average tumor size at the beginning of the study was 78 mm³. The average body weight at the beginning of the study was 27.20 g. Mice in all the groups gained weight and by the end of the study the weights of mice in the various groups were increased by 20 to 25% of their pretreatment weight. The study was terminated on day 57, when a majority of the animals either had ulcerated tumors or had a tumor volume of over 1500 mm³.

Tables 2 and 3, below, summarize the final results seen on day 49 of the study (last day of 100% survival of control animals), and provide a group survival comparison between the Adagen® treated animals and the Avastin® treated animals. Tumors in the control group grew steadily throughout the study. On day 49, the mean tumor volume size was 783.1 (±556.2) mm³. The percent change in tumor growth was 833.3% (±622.7). Treatment with Adagen® at all the three dose levels was effective in inhibiting tumor growth. It should be noted that for all the treatment groups, the tumors grew at a slow rate until the last day of dosing (day 33), after which the tumors had a faster rate of growth (data not shown). Consistent with this observation is the fact that the % change in tumor volume at all of the three dose levels of Adagen® was significantly different from that of the control group until day 36 (P<0.05) (data not shown).

This suggests that Adagen® has a cytostatic effect on tumor growth. Although the % change in tumor volume was not statistically different from that of controls after day 36 until the end of the study, treatment with Adagen® resulted in detectable tumor growth inhibition. In particular, tumors treated with 2000 IU/kg Adagen® had average tumor volume of 343.0 (±249.8) mm$^3$ on day 49. The average change in tumor volume was 424.2% (±360.6). Adagen® at 2000 IU/kg showed 56% tumor growth inhibition.

The tumors treated with 500 IU/kg Adagen® had a mean tumor volume of 696.3 (±290.4) mm$^3$ on day 49. The average change in tumor volume was 797.6% (±492.7), and the change from the initial tumor was 897.6% (±492.7). Tumor growth inhibition was 11.1%. Tumors in this group had similar tumors growth rates as the other Adagen® treated groups until day 40 after which they grew at a much faster rate. The reason for this discrepancy is unknown.

The tumors treated with 100 IU/kg Adagen® had a mean tumor volume of 414.8 (±219.0) mm$^3$ on day 49. The average change in tumor volume was 489.9% (±307.0), and the average percent change from the initial tumor was 589.9% (±307.0). Tumor growth inhibition or TGI was 47.0%.

The therapeutic effect of Adagen® reached a maximal effect at the lowest dose of 100 IU/kg. It should be noted that 100 IU/kg dose approximates the clinical human dose of Adagen® (dose used to treat SCID children). Avastin® showed the most effective decrease in tumor size with a tumor growth inhibition or TGI of 92.5%.

In conclusion, treatment with Adagen® at all the three dose levels was effective in inhibiting growth of DU145 tumors in vivo.

Example 2

Antitumor Efficacy of Adagen® in SK-OV-3 Human Ovarian Tumor Xenograft Model

A) Test System

| | |
|---|---|
| Species: | Mice, *Mus musculus* |
| Strain: | Athymic nude |
| Supplier: | Harlan-Sprague Dawley |
| Sex: | Female |
| Mean Initial Weight: | 22.18 g |
| No. on Study: | 54 |
| Acclimation Period: | 7 days following arrival |

B) Methods
Experimental Design:

SK-OV-3 human ovarian adenocarcinoma tumors were established in nude mice by subcutaneous injection of 3×10$^6$ cells/mouse into the right axillary flank. Tumor growth was monitored twice weekly and measured once palpable. The tumor volume for each mouse was determined by measuring two dimensions with calipers and calculated using the formula: tumor volume=(length×width$^2$)/2). When tumors reach an average volume of 90 mm$^3$, the mice were divided into experimental groups (9/group). The experimental groups were set up as shown in the table below. The first day of dosing was designated as Day 1. Mouse weight and tumor size were measured at the beginning of the study and twice

TABLE 2

Final Summary (Day 49)

| Group No. | Compound | Final Tumor Volume Means | Final Tumor Volume Medians | % Change in Tumor Volume | % Initial Tumor Volume | % Initial Tumor Volume | # of Regressions | # Cured | % Survival |
|---|---|---|---|---|---|---|---|---|---|
| 1 | Saline | 783.1 (556.2) | 680.0 | 833.3 (622.7) | 933.3 (622.7) | — | 0 | 0 | 62.5 |
| 2 | Adagen (2000 IU/kg) | 343.0 (249.8) | 283.8 | 424.2 (360.6) | 524.2 (360.6) | 56.2 | 0 | 0 | 75.0 |
| 3 | Adagen (500 IU/kg) | 696.3 (290.4) | 766.2 | 797.6 (492.7) | 897.6 (492.7) | 11.1 | 0 | 0 | 75.0 |
| 4 | Adagen (100 IU/kg) | 414.8 (219.0) | 349.8 | 489.9 (307.0) | 589.9 (307.0) | 47.0 | 0 | 0 | 75.0 |
| 5 | Avastin (5 mg/kg) | 58.5 (36.1) | 49.3 | −15.7 (59.6) | 84.3 (59.6) | 92.5 | 7/8 | 0 | 87.5 | regression, # cured and % survival data are from day 56.

TABLE 3

Group Survival Comparison (# Animal Live)

| Group | 1 | 5 | 8 | 12 | 15 | 19 | 22 | 26 | 29 | 33 | 36 | 40 | 43 | 49 | 51 | 55 | 57 |
|---|---|---|---|---|---|---|---|---|---|---|---|---|---|---|---|---|---|
| 1: Saline | 8 | 8 | 8 | 8 | 8 | 8 | 8 | 8 | 8 | 8 | 8 | 8 | 8 | 5[α] | 5 | 5 | 5 |
| 2: Adagen (2000 U/kg) | 8 | 8 | 8 | 8 | 8 | 8 | 8 | 8 | 8 | 8 | 8 | 7[ε] | 7 | 6[η] | 6 | 6 | 6 |
| 3: Adagen (500 U/kg) | 8 | 8 | 8 | 8 | 8 | 8 | 8 | 8 | 8 | 8 | 8 | 7[ε] | 7 | 6[η] | 6 | 5[i] | 5 |
| 4: Adagen (100 U/kg) | 8 | 8 | 8 | 8 | 8 | 8 | 8 | 8 | 8 | 8 | 8 | 6[β] | 6 | 6 | 6 | 5[i] | 5 |
| 5: Avastin (5 mg/kg) | 8 | 8 | 8 | 8 | 8 | 8 | 8 | 8 | 8 | 8 | 8 | 8 | 8 | 7[η] | 7 | 7 | 7 |

[α]Two animals were sacrificed due to tumor sizes in excess of 1500 mm$^3$. One animal sacrificed due to an ulcerated tumor.
[ε]Animal sacrificed due to an ulcerated tumor on day 40.
[η]Animal sacrificed due to an ulcerated tumor on day 49.
[i]Animal sacrificed due to an ulcerated tumor on day 55.
[β]Two animals were sacrificed due to ulcerated tumors on day 49.

weekly until termination of the study. The study was terminated after approximately 7 weeks (52 days), when majority of animals had large or ulcerated tumor masses.

TABLE 4

| Group # | Group | # mice (n) | Dose (U/kg) | Route of injection | Dosing schedule |
|---|---|---|---|---|---|
| 1 | Control | 9 | saline | i.p | Twice weekly × 5 |
| 2 | Adagen ® | 9 | 2000 | i.p | Twice weekly × 5 |
| 3 | Adagen ® | 9 | 500 | i.p | Twice weekly × 5 |
| 4 | Adagen ® | 9 | 100 | i.p | Twice weekly × 5 |
| 5 | Avastin ® | 9 | 100 ug/mouse | i.p | Twice weekly × 5 |
| 6 | Native ADA | 9 | 2000 | i.p. | Twice weekly × 5 |

Dosing Regimen:
Adagen ®, Avastin ®, or Native ADA was administered intravenously twice weekly for five weeks (total: 10 doses).
Test Articles:
Adagen ®: Lot Number: NV0604, Concentration: 229 IU/ml
Avastin ®: Lot Number: M66781, Concentration: 25 mg/ml
Native ADA: Lot Number: 06-0315-111

Dose Calculations:
Based on body weight taken on day 1.
Clinical Examinations:
The mice were examined visually upon arrival. Thereafter, mice were individually examined twice a week following initial tumor palpation, for clinical signs, general behavioral changes, and monitored for body weight. Any death and clinical sign were recorded. Food and water consumption was not monitored. Mice bearing tumors that showed open necrotic lesions were sacrificed. Mice losing more than 20% of body weight were also humanely sacrificed.
Statistical Analysis:
Differences in % change in tumor volume between various treatments were compared using one-way analysis of variance. All pairwise multiple comparisons were made using the Tukey-Kramer method.
C) Results
Definitions of the Terms Used:
(a) % of Initial tumor volume: (Tumor volume on any given day/Tumor volume on Day 1)×100
(b) % change in tumor volume: [(Tumor volume on any given day-Tumor volume on Day 1)/Tumor volume on day 1]×100
(c) % Tumor growth inhibition (TGI): [(Mean tumor volume of control group-Mean tumor volume of treatment group)/Mean tumor volume of control group]×100
(d) Regression of tumor is defined as negative tumor volume compared to day 1

(e) Cure is defined as complete absence of tumor as observed from naked human eye The average tumor size at the beginning of the study was 90 mm$^3$. The average body weight at the beginning of the study was 22.2 g. The mean body weight in all the groups did not change significantly throughout the study. The study was terminated on day 52. Four of the mice were sacrificed due to tumors growing over 1500 mm$^3$.

Table 5, below, gives the final summary of results as on day 32 (last day of 66% survival of control animals). Tumors in the control group grew steadily throughout the study. On day 32, the mean tumor volume size was 754.9 (±700.7) mm$^3$. The percent change in tumor growth was 693.2% (±673.6) mm$^3$.

TABLE 5

Final Summary (Day 32)

| Group No. | Compound | Final Tumor Volume Means | Final Tumor Volume Medians | % Change in Tumor Volume | % Initial Tumor Volume | % Initial Tumor Volume | # of Regressions | # Cured | % Survival |
|---|---|---|---|---|---|---|---|---|---|
| 1 | Saline | 754.9 (700.7) | 485.5 | 693.2 (673.6) | 793.2 (673.6) | — | 0 | 0 | 66 |
| 2 | Adagen ® (2000 IU/kg) | 437.7 (122.2) | 446.4 | 402.1 (177.7) | 502.1 (177.7) | 42.0 | 0 | 0 | 100 |
| 3 | Adagen ® (500 IU/kg) | 471.1 (60.0) | 465.8 | 421.3 (102.2) | 521.3 (102.2) | 37.6 | 0 | 0 | 89 |
| 4 | Adagen ® (100 IU/kg) | 497.7 (152.6) | 478.9 | 450.7 (172.7) | 550.7 (172.7) | 34.1 | 0 | 0 | 100 |
| 5 | Avastin ® (5 mg/kg) | 210.2 (65.9) | 198.6 | 161.6 (88.3) | 261.6 (88.3) | 72.2 | 0 | 0 | 100 |
| 6 | Native ADA (2000 IU/kg) | 356.6 (213.0) | 329.7 | 340.1 (239.1) | 440.1 (239.1) | 52.8 | 0 | 0 | 77 |

Tumors treated with 2000 IU/kg Adagen® had average tumor volume of 437.7 (122.2) mm$^3$ on day 32. The average change in tumor volume was 402.1% (177.7). Adagen® at 2000 IU/kg showed 42% tumor growth inhibition.

The tumors treated with 500 IU/kg Adagen® had a mean tumor volume of 471.1 (±60.0) mm$^3$ on day 32. The average change in tumor volume was 421.3% (±102.2), and the change from the initial tumor was 521.3% (±102.2). Tumor growth inhibition was 37.6%.

The tumors treated with 100 IU/kg Adagen® had a mean tumor volume of 497.7 (152.6) mm$^3$ on day 32. The average change in tumor volume was 450.7% (±172.7), and the average percent change from the initial tumor was 550.7% (±172.7). Tumor growth inhibition was 34.1%.

The tumors treated with 2000 IU/kg Native ADA had a mean tumor volume of 356.6 (213.0)mm$^3$ on study day 32. The average change in tumor volume was 340.1% (±210.0), and the average percent change from the initial tumor was 440.1% (239.1). Tumor growth inhibition was 52.8%.

Treatment with Adagen® at either dose level was commensurate with the results from controls. However, Adagen® at each dose level produced TGI as noted above.

The therapeutic effect of Adagen® reached a maximal effect at the lowest dose of 100 IU/kg. It should be noted that 100 IU/kg dose approximates with the clinical human dose of Adagen® (dose used to treat SCID children). Avastin®, serving as a positive control in this study, showed the most effective decrease in tumor size with a TGI of 72%.

In conclusion, treatment with Adagen® at 100, 500 or 2000 IU/kg resulted in tumor growth inhibition ranging from 34-42%.

Alternative recombinant ADA enzymes for the inventive methods are described, as follows.

Example 3

Construction of *E. coli* Expression Strain Expressing Recombinant Human ADA with a Cys to Ser Change at Position 74 of the Mature Protein The reported 363 amino acid sequence of human adenosine deaminase (GenBank NP_000013, incorporated by reference herein) was analyzed for the presence of cysteine codons. Five positions in the mature (N-terminal Met is cleaved) polypeptide encode cysteine (C74, C152, C153, C168, C261). In the designed and modified gene expressing human ADA, only one of these five cysteine codons (Cysteine 74, TGC) was changed to a serine codon (TCC) (this is position 75 in the translated protein). The defined polypeptide sequence (see SEQ ID NO: 3) was provided to Blue Heron Corporation (Bothell, Wash., U.S.A.) for whole gene synthesis of a new gene having codons optimized for expression in *E. coli*, using standard chemical synthesis of overlapping oligonucleotide segments. In brief, the sequence was optimized for bacterial expression by following the standard bacterial codon usage for *Escherichia coli* K12, using the codon data described by Grantham R. et al.; 1981; "Codon catalogue usage in genome strategy modulated for gene expressivity," *Nucleic Acid Res.* 9:r43-r47, and Lathe, R. 1985; "Synthetic oligonucleotide probes deduced from amino acid sequence data, Theoretical and practical considerations." *J. Mol Biol;* 183:1-12.

The corresponding RNA sequence was then analyzed for the formation of hairpin structure or loop formation and was subjected to minimum free energy calculations. The flanking restriction sites, NdeI and BamHI were included at the termini of the gene. Following digestion of the synthetic DNA with the restriction enzymes NdeI and BamHI the 1.1 kilobase gene was ligated via T4 DNA ligase into the plasmid vector pET-28a (Novagen Corporation), which had also been digested with these two enzymes. The recombinant plasmid was introduced into *E. coli* strain BLR (DE3) or HMS174 (DE3) by electroporation using a BTX Electro Cell Manipulator 600 according to the manufacturer's instructions. The transformation mixture was plated on LB agar plates containing kanamycin (15 μg/ml) in order to allow for selection of colonies containing the plasmid pET-28a/ADAcysSer (designated ADAc75s/pET28a: BLR(DE3) or ADAc75s/pET28a:HMS 174(DE3)). The ADA variant gene nucleotide sequence was verified by DNA sequence analysis with a ABI Prism 310 Genetic Analyzer using Big Dye Terminators. The DNA sequence encoding the $Ser_{74}$-rhADA open reading frame is according to SEQ ID NO: 4.

Isolated colonies were further purified by plating and analyzed for IPTG inducible gene expression in LB medium by standard methods such as those described in Novagen pET System Manual Ninth Edition, incorporated by reference herein.

Several induction parameters were examined including time, temperature and inducer concentration. A preferred condition was induction with 50 μM IPTG for 12 hrs at 25° C., which allowed high level production of ADA within the cytoplasm of the host bacteria at about 20% of total cell protein.

The expressed ADA protein was confirmed on SDS PAGE analysis to exhibit the correct molecular weight of approximately 40 kDa (data not shown).

Example 4

Construction of *E. coli* Expression Strain Expressing Recombinant Bovine ADA with a Cys to Ser Change at Position 74 of the Mature Protein The purified mature ADA protein derived from bovine intestinal preparations is a 356 amino acid protein lacking the N-terminal methionine and also lacking the final six C-terminal residues predicted from the cDNA sequence (GenBank NP_776312, incorporated by reference herein). The bovine ADA amino acid sequence was analyzed for the presence of cysteine codons. Five positions in the mature polypeptide encode cysteine (C74, C152, C153, C168, C261). In the designed and modified bovine ADA synthetic gene, only one of these five cysteine positions (cysteine 74) was changed to a serine residue. This was performed by inserting a serine codon (TCC) in place of the normal cysteine codon at position 74 of the mature polypeptide (or position 75 of the translation product). The gene was also codon optimized for expression in *E. coli*.

In brief, the defined polypeptide sequence (see SEQ ID NO: 1) was provided to BioCatalytics Inc. for whole gene synthesis of a new gene having codons optimized for expression in *E. coli*, using their methods that include chemical synthesis of overlapping oligonucleotide segments. The BioCatalytics methods are described in greater detail by U.S. Pat. No. 6,366,860, the contents of which are incorporated by reference herein in their entirety.

Bovine ADA expression was investigated in several expression systems. For example, the flanking restriction sites, NdeI and BamHI were included at the termini of the gene. Following digestion of the synthetic DNA with the restriction enzymes NdeI and BamHI, the 1.1 kilobase gene was ligated via T4 DNA ligase into the plasmid vector pET-9d (Novagen Corporation), which had also been digested with these two enzymes. The recombinant plasmid was introduced into *E. coli* strain BLR (DE3) or HMS174 (DE3) by electroporation using a BTX Electro Cell Manipulator 600 according to the manufacturer's instructions. The transformation mixture was plated on LB agar plates containing kanamycin (15 μg/ml) to allow for selection of colonies containing the plasmid pET-9d/bADA (designated bADA/pET9d: BLR (DE3) or bADA/pET9d:HMS174(DE3)). The ADA variant gene nucleotide sequence was verified by DNA sequence analysis with a ABI Prism 310 Genetic Analyzer using Big Dye Terminators. The open reading frame of the DNA is shown by SEQ ID NO: 2.

Isolated colonies were further purified by plating and analyzed for IPTG inducible gene expression in LB medium by standard methods such as those described in Novagen pET System Manual Ninth Edition. Several induction parameters were examined including time, temperature and inducer concentration. A preferred condition was induction with 0.3% lactose for 12 hrs at 37° C., which allowed high level production of ADA within the cytoplasm of the host bacteria at about 20% of total cell protein. The ADA product was confirmed on SDS PAGE analysis to exhibit the correct molecular weight of approximately 40 kDa.

Example 5

Purification of Recombinant Human Mutein ADA Protein

The purification of rhADA was carried out in a 3 chromatographic protocol developed by Enzon. Bacterial fermentation was conducted for *E. coli* expressing the rhADA protein from a synthetic gene on plasmid pET28a (Novagen) in host cell HMS174(DE3). Rifampicin (200 µg/ml) and kanamycin (30 µg/ml) were included in a minimal glycerol medium supplemented with yeast extract (30 g/l) and the cells were grown at 28° C. to an $OD_{600}$ of 11 when the inducer IPTG was added to 5 mM final concentration. After 40 hours ($OD_{600}$~110), the cells were harvested by centrifugation and frozen at −20° C. Briefly, thawed cell paste (50 g) was re-suspended in 1800 ml buffer of 10 mM Tris, 1 mM DTT, pH 8.0, and homogenized at 1200 RPM for 10 seconds with Tempest Virtis (Sentry™, Microprocessor, Boston, Mass.). This suspension was passed through a stainless steel mesh (Opening micrometer 250µ, No. 60, W.S Tyler) to remove big particles. The homogenous cell suspension was microfluidized for 3 cycles at 15,000 psi (unit was ice-bathed) (Micro Fluidizer, Microfluidics Corp., Model#110Y, Boston, Mass.). At the end of micro fluidization, 200 ml of the same buffer as above was used to rinse the unit and this solution was combined with the above suspension. The soluble protein from cell lysates was extracted by centrifugation at 16,000 rpm for 40 minutes at 4° C. (Sorvall RC 5C plus, rotor SLA-1000). The supernatant was collected carefully to avoid unwanted mixing. The pH was adjusted to 8.0, and 1 mM $MgCl_2$ and 20 mg/mL DNase were added and incubated at room temperature for 2 hours. The pH was then adjusted to 6.5 with 1 N HCl. A second centrifugation was conducted as above, the supernatant collected, and adjusted to 2 mM EDTA, followed by filtration on Nalgene (90 mm filter unit). The volume of the filtered supernatant was 500 ml, total protein concentration by BCA method was 8.5 mg/ml.

The cell extract (100 ml) was adjusted to pH 7.2, 4.5 mS/cm and loaded onto HiTrap DEAE ff at 20 mM Bis-Tris, 20 mM NaCl, pH 6.5 and eluted with 20 mM Bis-Tris, 500 mM NaCl, pH 6.5. The peak fractions were identified by enzyme assay and SDS-PAGE and adjusted to 1.5 M ammonium sulfate in 20 mM $NaHPO_4$, pH 6.5 and loaded onto a HiTrap Phenyl ff column. The protein was eluted with a gradient of load buffer and 20 mM $NaHPO_4$, pH 6.5. The peak fraction (55 ml; 0.4 mg/ml) was diafiltered against 20 mM $NaHPO_4$, 1 mM EDTA, 1 mM DTT, pH 6.5 and loaded onto HiTrap SP-Sepharose ff and eluted with 20 mM $NaHPO_4$, 500 mM NaCl, 1 mM EDTA, 1 mM DTT, pH 6.5. The collected fraction contained purified ADA protein (77 ml; 0.1 mg/ml).

Example 6

Purification of Recombinant Bovine ADA Protein

The purification of rbADA expressed by the clone of Example 4 was carried out in a 3 chromatographic protocol developed by Enzon. Briefly, thawed cell paste (obtained from Blue Heron or Biocatalytics, respectively) of 200 g which was stored at −80° C. was re-suspended in 1800 ml buffer of 20 mM Bis-Tris, 1 mM EDTA, pH 7.4, and homogenized at 1200 RPM for 5 min with Tempest Virtis (Sentry™, Microprocessor, Boston, Mass.). This suspension was passed through a stainless steel mesh (Opening micrometer 250µ, No. 60, W.S Tyler) to removed big particles. The homogenous cell suspension was microfluidized for 3 cycles at 15,000 psi (unit was ice-bathed) (Micro Fluidizer, Microfluidics Corp., Model#110Y, Boston, Mass.). At the end of micro fluidization, 200 ml of the same buffer as above was used to rinse the unit and this solution was combined with the above suspension. The soluble protein from cell lysates was extracted by centrifugation at 7100 rpm (12000×g) for 60 minutes at 4° C. (Avanti J-201, Beckman Coulter; Rotor# JLA8.1000). The supernatant was collected carefully to avoid unwanted mixing.

To remove nucleotides in this cell extract, polyethyleneimine (PEI) was added to the above supernatant (final 0.15%, wt/v) and mixed thoroughly by stifling for 10 min. Then left this cell extract at 4° C. over night. The precipitant from this over night sample was removed by a centrifugation at 7100 rpm (12000×g), for 60 minutes at 4° C. (Avanti J-201, Beckman Coulter; Rotor# JLA8.1000). Similarly, the supernatant was collected carefully to avoid any unwanted mixing. To help ADA bind to the first column, 10% PEG4600 was added to this cell extract slowly and the pH of this cell extract was adjusted to 6.5 slowly with 1 N NaOH and 1N HCl. This supernatant was centrifuged again at 7100 rpm (12000×g), for 60 minutes at 4° C. (Avanti J-201, Beckman Coulter; Rotor# JLA8.1000) before loaded to the next column.

The cell extract was loaded to a pre-equilibrated Capto Q column (Cat#17-5316-01, GE Healthcare, Piscataway, N.J. Bed volume 350 ml pre packed in a XK-50 column) with a buffer of 20 mM Bis-Tris, 1 mM EDTA, pH 6.5. Before ADA was eluted off from the column at 80 mM NaCl in the equilibration buffer, elutions at 60 mM and 70 mM NaCl were first performed to remove impurities. The elution profile was analysed by ADA activity, SDS-PAGE analysis, Western Blots, and RP-HPLC.

After Capto Q column, 2 hydrophobic interaction chromatographic purifications were used one by one to further polish the purity of the protein. The first HIC was Octyl Sepharose 4FF (Cat#17-0946-02, GE Healthcare, Piscataway, N.J.). The pool of ADA fractions from Capto Q column was adjusted to 1.5 M $(NH_4)_2SO_4$ with ammonium sulfate powder directly and the pH was adjusted to 6.5. The filtered sample (Nalgene Nunc, CAT #540887, MEMB 0.2 PES, Rochester, N.Y.) was loaded to the 1$^{st}$ HIC column which was pre-equilibrated with 1.5 M $(NH_4)_2SO_4$, 20 mM potassium phosphate, 1 mM EDTA, pH 6.5 (Bed volume 150 ml, in XK-50, GE Healthcare, Piscataway, N.J.). The ADA protein was eluted with an ammonium sulfate gradient and the purity profile of this elution was determined by SDS-PACE and RP-HPLC. The ADA protein in the fractions of first HIC column was pooled and adjusted to 1 M $(NH_4)_2SO_4$ and loaded directly to the second HIC column (Bed volume 150 ml, XK-50, HIC Phenyl HP, Cat#17-1082-01, Piscataway, N.J.) which was pre-equilibrated with 1 M $(NH_4)_2SO_4$, 20 mM $KH_2PO_4$—$K_2HPO_4$, 1 mM EDTA, pH 6.5. ADA was eluted with ammonium sulfate gradient from 1 M to 300 mM in the 20 mM $KH_2PO_4$—$K_2HPO_4$, 1 mM EDTA, pH 6.5. ADA purity of these fractions were analyzed by SDS-PAGE and RP-HPLC. The purified rbADA or rhADA was further desalted and concentrated in a LabScale™ TFF systems (Membrane BioMax 5, Bedford, Mass.) against the storage buffer (for example, 100 mM sodium phosphate, 1 mM EDTA, pH 6.5).

Example 7

Preparation of PEGylated $Ser_{74}$-rbADA Via Urethane Linkage

SC-PEG (N-hydroxysuccinimidyl carbonate-activated polyethylene glycol, 0.084 mmol) is added to a solution of $Ser_{74}$-rbADA (0.00027 mmol) in 3 mL of sodium phosphate buffer (0.1 M, pH 7.8) with gentle stirring. The solution is stirred at 30° C. for 30 minutes. A GPC column (Zorbax GF-450) is used to monitor PEG conjugation. At the end of the reaction (as evidenced by the absence of native enzyme), the mixture is diluted with 12 mL of formulation buffer (0.05 M sodium phosphate, 0.85% sodium chloride, pH 7.3) and diafiltered with a Centriprep concentrator (Amicon) to remove the unreacted PEG. Dialfiltration is continued as needed at 4° C. until no more free PEG is detected by mixing equal amount of filtrate and 0.1% PMA (polymethacrylic acid in 0.1 M HCl).

Example 8

Preparation of PEGylated $Ser_{74}$-rhADA Via Urethane Linkage

SC-PEG (0.084 mmol) is reacted with $Ser_{74}$-rhADA (0.00027 mmol) using the same conditions as described in Example 7.

Example 9

Preparation of PEGylated $Ser_{74}$-rbADA via Amide Linkage

SS-PEG (N-hydroxysuccinimidyl succinate-activated polyethylene glycol, 0.084 mmol) is added to a solution of $Ser_{74}$-rbADA (0.00027 mmol) in 3 mL of sodium phosphate buffer (0.1 M, pH 7.8) with gentle stirring. The solution is stirred at 30° C. for 30 minutes. A GPC column (Zorbax GF-450) is used to monitor PEG conjugation. At the end of the reaction (as evidenced by the absence of native enzyme), the mixture is diluted with 12 mL of formulation buffer (0.05 M sodium phosphate, 0.85% sodium chloride, pH 7.3) and diafiltered with a Centriprep concentrator (Amicon) to remove the unreacted PEG. Dialfiltration is continued as needed at 4° C. until no more free PEG is detected by mixing equal amount of filtrate and 0.1% PMA (polymethacrylic acid in 0.1 M HCl).

Example 10

Preparation of PEGylated Mutein rhADA via Amide Linkage

SS-PEG (0.084 mmol) is reacted with mutein rhADA (0.00027 mmol) using the same conditions as described in Example 9.

We claim:

1. A method of treating a patient having a tumor or cancer of the prostate or ovaries comprising administering an effective amount of adenosine deaminase to the patient in need thereof, wherein the adenosine deaminase is adenosine deaminase purified from a bovine source or is a recombinant bovine adenosine deaminase according to SEQ ID NO: 5 or SEQ ID NO: 1, or is a recombinant bovine adenosine deaminase according to SEQ ID NO: 1 or SEQ ID NO: 5, with an amino acid substitution selected from the group consisting of Gln in place of $Lys_{198}$; Ala in place of $Thr_{245}$; Arg in place of $Gly_{351}$ and combinations thereof;

wherein the adenosine deaminase is conjugated to polyethylene glycol; and wherein the polyethylene glycol ranges in size from about 4,000 to about 45,000 Daltons.

2. The method of claim 1, wherein the tumor or cancer is malignant.

3. The method of claim 1, wherein the amount of conjugated adenosine deaminase administered is effective to substantially reduce tissue levels of adenosine or deoxyadenosine in said patient, and wherein growth or spread of the tumor is inhibited by reduced tissue levels of adenosine in said patient.

4. The method of claim 1, wherein the tumor or cancer is a solid tumor or cancer.

5. The method of claim 1, wherein the conjugated adenosine deaminase is administered in a dose ranging from about 10 U to about 30 U of adenosine deaminase per kg.

6. The method of claim 1, wherein the conjugated adenosine deaminase is administered for a sufficient period of time to maintain inhibition of the tumor.

7. The method of claim 1, wherein the conjugated adenosine deaminase is administered for a time period ranging from 1 to about 20 days.

8. The method of claim 1, wherein the conjugated adenosine deaminase comprises two or more molecules of adenosine deaminase per polyethylene glycol.

9. The method of claim 1, wherein the conjugated adenosine deaminase comprises from about 11 to about 18 polyethylene glycol strands attached to epsilon amino groups of one or more Lys residues of the adenosine deaminase.

10. The method of claim 1, wherein the adenosine deaminase is conjugated to the polyethylene glycol via a urethane linkage.

11. The method of claim 1, wherein the conjugated adenosine deaminase is administered by a route selected from the group consisting of subcutaneous, intravenous, intramuscular, intrathecal, intraperitoneal, inhalation and transurethral.

12. The method of claim 1, wherein the recombinant adenosine deaminase comprises the sequence of SEQ ID NO: 5.

13. The method of claim 1, wherein the recombinant bovine adenosine deaminase comprising SEQ ID NO: 5 further comprises a Cys74 that is capped to prevent oxidation in an aqueous medium.

14. The method of claim 1, wherein the tumor or cancer is a prostate tumor or cancer.

15. The method of claim 1, wherein the tumor or cancer is an ovarian tumor or cancer.

16. The method of claim 1, wherein the conjugated adenosine deaminase is ADAGEN®.

17. The method of claim 1, wherein the polyethylene glycol is about 5,000 Daltons.

18. The method of claim 1, wherein the recombinant adenosine deaminase comprises the sequence of SEQ ID NO: 1.

19. The method of claim 1, wherein the recombinant adenosine deaminase is according to SEQ ID NO: 1 or SEQ ID NO: 5, with an amino acid substitution selected from the group consisting of Gln in place of $Lys_{198}$; Ala in place of $Thr_{245}$; Arg in place of $Gly_{351}$ and combinations thereof.

* * * * *

SEQUENCE LISTING

```
<160> NUMBER OF SEQ ID NOS: 5

<210> SEQ ID NO 1
<211> LENGTH: 356
<212> TYPE: PRT
<213> ORGANISM: Bovine
<220> FEATURE:
<221> NAME/KEY: misc_feature
<222> LOCATION: (74)..(74)
<223> OTHER INFORMATION: Cys to Ser mutein

<400> SEQUENCE: 1

Ala Gln Thr Pro Ala Phe Asn Lys Pro Lys Val Glu Leu His Val His
1               5                   10                  15

Leu Asp Gly Ala Ile Lys Pro Glu Thr Ile Leu Tyr Tyr Gly Arg Lys
            20                  25                  30

Arg Gly Ile Ala Leu Pro Ala Asp Thr Pro Glu Glu Leu Gln Asn Ile
        35                  40                  45

Ile Gly Met Asp Lys Pro Leu Ser Leu Pro Glu Phe Leu Ala Lys Phe
    50                  55                  60

Asp Tyr Tyr Met Pro Ala Ile Ala Gly Ser Arg Glu Ala Val Lys Arg
65                  70                  75                  80

Ile Ala Tyr Glu Phe Val Glu Met Lys Ala Lys Asp Gly Val Val Tyr
                85                  90                  95

Val Glu Val Arg Tyr Ser Pro His Leu Leu Ala Asn Ser Lys Val Glu
            100                 105                 110

Pro Ile Pro Trp Asn Gln Ala Glu Gly Asp Leu Thr Pro Asp Glu Val
        115                 120                 125

Val Ser Leu Val Asn Gln Gly Leu Gln Glu Gly Glu Arg Asp Phe Gly
    130                 135                 140

Val Lys Val Arg Ser Ile Leu Cys Cys Met Arg His Gln Pro Ser Trp
145                 150                 155                 160

Ser Ser Glu Val Val Glu Leu Cys Lys Lys Tyr Arg Glu Gln Thr Val
                165                 170                 175

Val Ala Ile Asp Leu Ala Gly Asp Glu Thr Ile Glu Gly Ser Ser Leu
            180                 185                 190
```

```
Phe Pro Gly His Val Lys Ala Tyr Ala Glu Ala Val Lys Ser Gly Val
        195                 200                 205
His Arg Thr Val His Ala Gly Glu Val Gly Ser Ala Asn Val Val Lys
    210                 215                 220
Glu Ala Val Asp Thr Leu Lys Thr Arg Leu Gly His Gly Tyr His
225                 230                 235                 240
Thr Leu Glu Asp Thr Thr Leu Tyr Asn Arg Leu Arg Gln Glu Asn Met
                245                 250                 255
His Phe Glu Val Cys Pro Trp Ser Ser Tyr Leu Thr Gly Ala Trp Lys
            260                 265                 270
Pro Asp Thr Glu His Pro Val Val Arg Phe Lys Asn Asp Gln Val Asn
        275                 280                 285
Tyr Ser Leu Asn Thr Asp Asp Pro Leu Ile Phe Lys Ser Thr Leu Asp
    290                 295                 300
Thr Asp Tyr Gln Met Thr Lys Asn Glu Met Gly Phe Thr Glu Glu
305                 310                 315                 320
Phe Lys Arg Leu Asn Ile Asn Ala Ala Lys Ser Ser Phe Leu Pro Glu
                325                 330                 335
Asp Glu Lys Lys Glu Leu Leu Asp Leu Leu Tyr Lys Ala Tyr Gly Met
            340                 345                 350

Pro Ser Pro Ala
        355

<210> SEQ ID NO 2
<211> LENGTH: 1074
<212> TYPE: DNA
<213> ORGANISM: Bovine

<400> SEQUENCE: 2
atggctcaga cccccggcttt caacaaaccg aaggtagaac tgcacgtaca cctggatggt      60
gctatcaaac cggagactat cctgtactat ggtcgtaagc gtggcatcgc tctgccggct     120
gacactccgg aagaactgca gaacatcatc ggcatggaca aaccgctgtc tctgccggaa     180
ttcctggcta aattcgacta ctacatgccg gctatcgctg ttctcgtga agcagtcaaa      240 cgtatcgctt acgaattcgt agaaatgaaa gctaagatg gtgtagtata cgttgaagtt      300
cgttactctc gcacctgct ggcaaactct aaagttgaac cgatcccgtg aaccaggca      360 gaaggcgatc tgactccgga tgaagtagtt tctctggtta accagggtct gcaggagggt      420
gaacgcgatt tcggcgtaaa agttcgttct atcctgtgct gcatgcgcca ccagccgtct      480
tggtcttctg aagttgttga actgtgcaag aaataccgtg agcagaccgt agttgctatc      540
gatctggcag gtgatgaaac catcgaaggt tcttctctgt tccgggtca cgtaaaggct      600 tatgctgaag ctgttaaatc tggcgtacac cgtactgtac acgcaggtga agttggttct      660
gctaacgttg ttaagaagc tgttgacacc ctgaaaactg aacgcctggg tcacggctac      720 cacacccctgg aagacaccac cctgtacaac cgtctgcgtc aggaaaacat gcacttcgaa      780
gtttgtccgt ggtcctctta cctgactggt gcttggaaac cggacaccga cacccggtt      840 gttcgtttca aaacgacca ggtaaactac tctctgaaca ctgacgatcc gctgatcttc      900
aaatctaccc tggacaccga ctaccagatg accaaaaacg aaatgggttt cactgaagaa      960
gaattcaaac gtctgaacat caacgctgct aagtcctctt ttctgccgga agatgagaaa     1020
aaagaactgc tggacctgct gtacaaggca tacggtatgc cgtctccggc ttaa           1074
```

```
<210> SEQ ID NO 3
<211> LENGTH: 362
<212> TYPE: PRT
<213> ORGANISM: Human
<220> FEATURE:
<221> NAME/KEY: misc_feature
<222> LOCATION: (74)..(74)
<223> OTHER INFORMATION: Cys to Ser mutein

<400> SEQUENCE: 3

Ala Gln Thr Pro Ala Phe Asp Lys Pro Lys Val Glu Leu His Val His
1               5                   10                  15

Leu Asp Gly Ser Ile Lys Pro Glu Thr Ile Leu Tyr Tyr Gly Arg Arg
                20                  25                  30

Arg Gly Ile Ala Leu Pro Ala Asn Thr Ala Glu Gly Leu Leu Asn Val
            35                  40                  45

Ile Gly Met Asp Lys Pro Leu Thr Leu Pro Asp Phe Leu Ala Lys Phe
50                  55                  60

Asp Tyr Tyr Met Pro Ala Ile Ala Gly Ser Arg Glu Ala Ile Lys Arg
65                  70                  75                  80

Ile Ala Tyr Glu Phe Val Glu Met Lys Ala Lys Glu Gly Val Val Tyr
                85                  90                  95

Val Glu Val Arg Tyr Ser Pro His Leu Leu Ala Asn Ser Lys Val Glu
                100                 105                 110

Pro Ile Pro Trp Asn Gln Ala Glu Gly Asp Leu Thr Pro Asp Glu Val
            115                 120                 125

Val Ala Leu Val Gly Gln Gly Leu Gln Glu Gly Glu Arg Asp Phe Gly
130                 135                 140

Val Lys Ala Arg Ser Ile Leu Cys Cys Met Arg His Gln Pro Asn Trp
145                 150                 155                 160

Ser Pro Lys Val Val Glu Leu Cys Lys Lys Tyr Gln Gln Thr Val
                165                 170                 175

Val Ala Ile Asp Leu Ala Gly Asp Glu Thr Ile Pro Gly Ser Ser Leu
            180                 185                 190

Leu Pro Gly His Val Gln Ala Tyr Gln Glu Ala Val Lys Ser Gly Ile
                195                 200                 205

His Arg Thr Val His Ala Gly Glu Val Gly Ser Ala Glu Val Val Lys
            210                 215                 220

Glu Ala Val Asp Ile Leu Lys Thr Glu Arg Leu Gly His Gly Tyr His
225                 230                 235                 240

Thr Leu Glu Asp Gln Ala Leu Tyr Asn Arg Leu Arg Gln Glu Asn Met
                245                 250                 255

His Phe Glu Ile Cys Pro Trp Ser Ser Tyr Leu Thr Gly Ala Trp Lys
            260                 265                 270

Pro Asp Thr Glu His Ala Val Ile Arg Leu Lys Asn Asp Gln Ala Asn
            275                 280                 285

Tyr Ser Leu Asn Thr Asp Asp Pro Leu Ile Phe Lys Ser Thr Leu Asp
            290                 295                 300

Thr Asp Tyr Gln Met Thr Lys Arg Asp Met Gly Phe Thr Glu Glu Glu
305                 310                 315                 320

Phe Lys Arg Leu Asn Ile Asn Ala Ala Lys Ser Ser Phe Leu Pro Glu
                325                 330                 335

Asp Glu Lys Arg Glu Leu Leu Asp Leu Leu Tyr Lys Ala Tyr Gly Met
            340                 345                 350

Pro Pro Ser Ala Ser Ala Gly Gln Asn Leu
            355                 360
```

<210> SEQ ID NO 4
<211> LENGTH: 1089
<212> TYPE: DNA
<213> ORGANISM: Human

<400> SEQUENCE: 4

```
atggctcaga cacccgcatt tgataaaccg aaagtggaac tgcatgtcca cctggatggt      60
agcatcaaac cggaaactat cttatattac ggtcggcgtc gtggtattgc gttgccggca     120
aacacggctg aaggtttgct gaacgtgatc ggcatggaca accgctgac cttgccggat      180
tttttggcga aatttgatta ttatatgccg gcgattgctg gttcccgcga ggcaatcaaa     240
cgcatcgcgt atgagtttgt tgaaatgaaa gcgaaagaag gcgttgtgta tgttgaggtc     300
cgttacagtc cgcatctgct ggctaacagc aaggtagaac ctatcccctg gaaccaagct     360
gaaggcgatc tgacgccgga tgaagtggtt gctctggtgg gtcagggttt acaggagggg    420
gagcgcgatt ttggcgttaa agctcgctct attttatgtt gcatgcgcca tcagcccaat     480
tggtccccga aagtggttga actttgtaaa agtaccaac aacagaccgt tgtcgcgatt      540
gatttggcag gcgatgaaac aattccaggc agctccctgt tgccagggca cgtgcaagcg    600
taccaagaag cagtgaaaag cggcatccac cggactgtcc acgccggcga ggtcggtagc    660
gccgaggttg tgaaagaagc cgtggacatc ctgaaaaccg agcggctggg ccatgggtac    720
cacacactgg aggatcaggc attatataac cgcttacgcc aggaaaatat gcatttcgaa    780
atttgtccgt ggagtagtta cttaactggc gcgtggaaac cggataccga acatgcggtt    840
atccgcttaa agaatgatca agcaaattac agtctgaata cagatgatcc cctgatttc     900
aagtctaccc tggacacaga ttatcagatg acgaagcggg atatgggatt tacggaagaa    960
gaatttaagc gtctcaatat caatgcggcg aaatcttcat ttctgccgga agatgagaaa   1020
cgtgagttgc tggatcttct gtacaaggcc tacggtatgc cgccgagcgc atcggccggg   1080
cagaaccctg                                                         1089
```

<210> SEQ ID NO 5
<211> LENGTH: 356
<212> TYPE: PRT
<213> ORGANISM: Bovine

<400> SEQUENCE: 5

Ala Gln Thr Pro Ala Phe Asn Lys Pro Lys Val Glu Leu His Val His
1               5                   10                  15

Leu Asp Gly Ala Ile Lys Pro Glu Thr Ile Leu Tyr Tyr Gly Arg Lys
            20                  25                  30

Arg Gly Ile Ala Leu Pro Ala Asp Thr Pro Glu Glu Leu Gln Asn Ile
        35                  40                  45

Ile Gly Met Asp Lys Pro Leu Ser Leu Pro Glu Phe Leu Ala Lys Phe
    50                  55                  60

Asp Tyr Tyr Met Pro Ala Ile Ala Gly Cys Arg Glu Ala Val Lys Arg
65                  70                  75                  80

Ile Ala Tyr Glu Phe Val Glu Met Lys Ala Lys Asp Gly Val Val Tyr
                85                  90                  95

Val Glu Val Arg Tyr Ser Pro His Leu Leu Ala Asn Ser Lys Val Glu
            100                 105                 110

Pro Ile Pro Trp Asn Gln Ala Glu Gly Asp Leu Thr Pro Asp Glu Val
        115                 120                 125

Val Ser Leu Val Asn Gln Gly Leu Gln Glu Gly Glu Arg Asp Phe Gly
    130                 135                 140

```
Val Lys Val Arg Ser Ile Leu Cys Cys Met Arg His Gln Pro Ser Trp
145                 150                 155                 160

Ser Ser Glu Val Val Glu Leu Cys Lys Lys Tyr Arg Glu Gln Thr Val
                165                 170                 175

Val Ala Ile Asp Leu Ala Gly Asp Glu Thr Ile Glu Gly Ser Ser Leu
            180                 185                 190

Phe Pro Gly His Val Lys Ala Tyr Ala Glu Ala Val Lys Ser Gly Val
        195                 200                 205

His Arg Thr Val His Ala Gly Glu Val Gly Ser Ala Asn Val Val Lys
    210                 215                 220

Glu Ala Val Asp Thr Leu Lys Thr Glu Arg Leu Gly His Gly Tyr His
225             230                 235                 240

Thr Leu Glu Asp Thr Thr Leu Tyr Asn Arg Leu Arg Gln Glu Asn Met
            245                 250                 255

His Phe Glu Val Cys Pro Trp Ser Ser Tyr Leu Thr Gly Ala Trp Lys
            260                 265                 270

Pro Asp Thr Glu His Pro Val Val Arg Phe Lys Asn Asp Gln Val Asn
        275                 280                 285

Tyr Ser Leu Asn Thr Asp Asp Pro Leu Ile Phe Lys Ser Thr Leu Asp
    290                 295                 300

Thr Asp Tyr Gln Met Thr Lys Asn Glu Met Gly Phe Thr Glu Glu Glu
305                 310                 315                 320

Phe Lys Arg Leu Asn Ile Asn Ala Ala Lys Ser Ser Phe Leu Pro Glu
                325                 330                 335

Asp Glu Lys Lys Glu Leu Leu Asp Leu Leu Tyr Lys Ala Tyr Gly Met
            340                 345                 350

Pro Ser Pro Ala
            355
```